United States Patent
Arvik et al.

(10) Patent No.: US 11,723,943 B2
(45) Date of Patent: *Aug. 15, 2023

(54) THERAPEUTIC USE OF CHARDONNAY SEED PRODUCTS

(71) Applicants: SONOMACEUTICALS, LLC, Santa Rosa, CA (US); THE UNITED STATES OF AMERICA, AS REPRESENTED BY THE SECRETARY OF AGRICULTURE, Washington, DC (US)

(72) Inventors: Torey James Arvik, Santa Rosa, CA (US); Rebecca Susan Lipson, Santa Rosa, CA (US); Wallace H. Yokoyama, Albany, CA (US)

(73) Assignees: SONOMACEUTICALS, LLC, Santa Rosa, CA (US); THE UNITED STATES OF AMERICA, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 182 days.

This patent is subject to a terminal disclaimer.

(21) Appl. No.: 17/020,533

(22) Filed: Sep. 14, 2020

(65) Prior Publication Data

US 2021/0236579 A1 Aug. 5, 2021

Related U.S. Application Data

(63) Continuation of application No. 16/145,595, filed on Sep. 28, 2018, now Pat. No. 10,772,924, which is a continuation of application No. 14/398,093, filed as application No. PCT/US2013/038696 on Apr. 29, 2013, now Pat. No. 10,105,409.

(60) Provisional application No. 61/798,992, filed on Mar. 15, 2013, provisional application No. 61/691,515, filed on Aug. 21, 2012, provisional application No. 61/640,622, filed on Apr. 30, 2012.

(51) Int. Cl.
*A61K 36/87* (2006.01)
*A61P 3/04* (2006.01)
*A61P 3/10* (2006.01)

(52) U.S. Cl.
CPC .............. *A61K 36/87* (2013.01); *A61P 3/04* (2018.01); *A61P 3/10* (2018.01)

(58) Field of Classification Search
None
See application file for complete search history.

(56) References Cited

U.S. PATENT DOCUMENTS

| | | | |
|---|---|---|---|
| 8,492,110 B2 | 7/2013 | Qi | |
| 10,105,409 B2 * | 10/2018 | Arvik | ............ A61K 36/87 |
| 10,744,177 B2 | 8/2020 | Arvik | |
| 10,772,924 B2 * | 9/2020 | Arvik | ............ A61P 3/10 |
| 2002/0192314 A1 | 12/2002 | Cho et al. | |
| 2006/0172012 A1 | 8/2006 | Finley et al. | |
| 2009/0082738 A1 | 3/2009 | Vad | |
| 2010/0260733 A1 | 10/2010 | Qi | |
| 2011/0217417 A1 | 9/2011 | Perlman | |
| 2017/0173102 A1 | 6/2017 | Arvik | |
| 2021/0187052 A1 | 6/2021 | Arvik | |

FOREIGN PATENT DOCUMENTS

| | | |
|---|---|---|
| AU | 1951200 A | 8/2001 |
| CN | 101277616 A | 10/2008 |
| DE | 202009013228 U1 | 2/2011 |
| WO | 2005048719 A1 | 6/2005 |
| WO | 2011039308 A3 | 5/2011 |
| WO | 2013165921 A2 | 11/2013 |
| WO | 2015164341 A1 | 10/2015 |

OTHER PUBLICATIONS

European Search Report for European Patent Application No. 15782906.0 dated Nov. 2, 2017.
International Search Report and Written Opinion for International PCT Application No. PCT/US2013/038696 dated Nov. 13, 2013.
Nakamura et al., "Analysis of Proanthocyanidins in Grape Seed Extract, Health Foods and Grape Seed Oils," A Journal of Health Sciences, Biochemistry, (Jan. 1, 2003) vol. 49, No. 1, pp. 45-54.
Notice of Allowance for U.S. Appl. No. 15/305,007 dated Apr. 9, 2020.
Park, "Effect of Grape Seed Extract (Vitis Vinifera) Supplementation on Antiobesity in C57BL/6J Mice," Dept. of Food Science and Human Nutrition, University of Cheonbuk (Korea), Feb. 2008, Dissertation Discussion pp. 39-44.
Tsang et al., "The Absorption, Metabolism and Excretion of Flavan-3-ols and Procyanidins Following the Ingestion of a Grape Seed Extract by Rats," British Journal of Nutrition (2005), 94, pp. 170-181.
Yilmaz et al., "Major Flavonoids in Grape Seed and Skins: Antioxidant Capacity of Catechin, Epicatechin, and Gallic Acid," J. Agric. Food Chem. (Jan. 28, 2004) vol. 52, No. 2, pp. 255-260.
Auger et al., "Polyphenols-enriched Chardonnay white wine and sparkling Pinot Noir red wine identically prevent early atherosclerosis in hamsters," J. Agric Food Chem (2005) 53(25):9823-9829.
Decorde et al., "Chardonnay grape seed procyanidin extract supplementation prevents high-fat diet-induced obesity in hamsters by improving adipokine imbalance and oxidative stress markers," Mol. Nutr. Foods Res. (2009) 53; (5):659-666.
Decorde et al., "Chardonnay grape seed procyanidins prevent obesity in hamsters," Agro Food Industry Hi-Tech; (2009)20(6):24-26.
Di Castelnuovo et al., Consumption of cocoa, tea and coffee and risk of cardiovascular disease, European Journal of Internal Medicine 2012 23:15-25.

(Continued)

Primary Examiner — Michael Barker
(74) Attorney, Agent, or Firm — Goodwin Procter LLP

(57) ABSTRACT

The present disclosure relates to health benefits of Chardonnay seed products.

18 Claims, 26 Drawing Sheets

Figure 1:
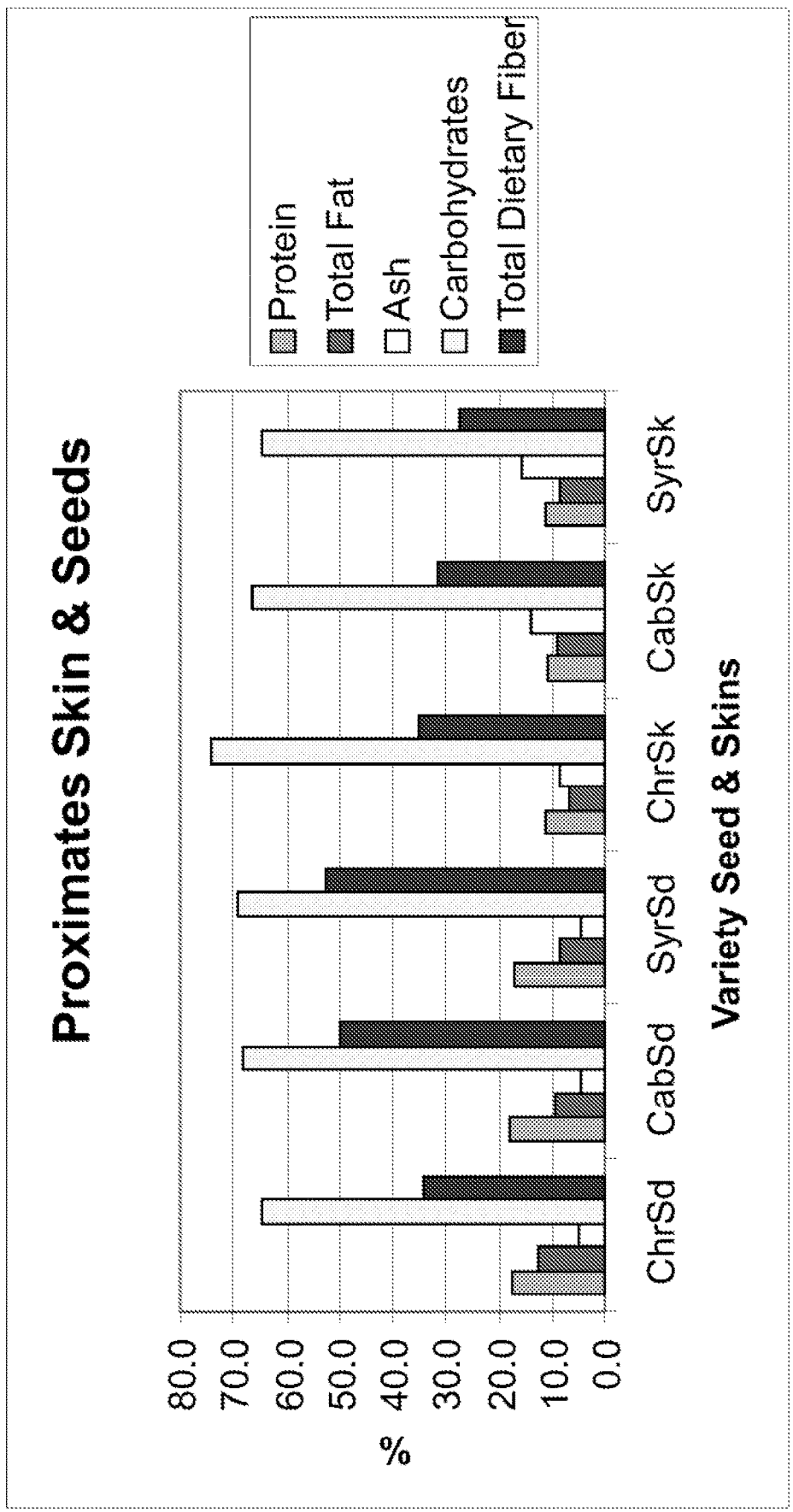

Specification includes a Sequence Listing.

(56) References Cited

OTHER PUBLICATIONS

Flechtner-Mors et al., "Effects of moderate consumption of white wine on weight loss in overweight and obese subjects," Int J Obes Relat Metab Disord (2004) 28(11):1420-1426.
Hogan et al., Dietary supplementation of grape skin extract improves glycemia and inflammation in diet-induced obese mice fed a western high fat diet, J Agric Food Chem 2011 59:3035-3041.
Hooper et al., Flavonoids, flavonoid-rich foods, and cardiovascular risk: a meta-analysis of randomized controlled trials, Am J Clin Nutr 2008 88:38-50.
International Search Report dated Jul. 6, 2015 for application No. PCT/US15/26825.
Jiao et al., Hypocholesterolemic activity of grape seed proanthocyanidin is mediated by enhancement of bile acid excretion and up-regulation of CYP7A1, J Nutri Biochem 2010 21:1134-1139.
Joosten et al., "Moderate alcohol consumption increases insulin sensitivity and ADIPOQ expression in postmenopausal women: a randomised, crossover trial," Diabetologia (2008) 51(8):1375-1381.
Kay, The future of flavonoid research, British Houmal of Nutrition 2010 104:S91-S95.
Keen et al., Cocoa antioxidants and cardiovascular health, Am J Clin Nutr 2005 81:298S-303S.
Kokavec et al., "Effect on plasma insulin and plasma glucose of consuming white wine alone after a meal," Alcohol Clin; Exp Res (2003) 27(11):1718-1723.
Landrault et al., "Antioxidant capacities and phenolics levels of French wines from different varieties and vintages," (2001) 49(7):3341-3348.
Landrault et al., "Effect of a polyphenols-enriched Chardonnay white wine in diabetic rats," J Argic Food Chem (2003); 51:311-318.
McCullough et al., Flavonoid intake and cardiovascular disease mortality in a prospective cohort of US adults, Am J Clin Nutr 2012 95:454-64.
Meyers et al., Influence of dietary quercetin on glutathione redox status in mice, J Agric Food Chem 2008 56:830-836.
Nijjar et al., Role of dietary supplements in lowering low-density lipoprotein cholesterol: a review, J Clin Lipid 2010 4:248-258.
Russo et al., The flavonoid quercetin in disease prevention and therapy: facts and fancies, Biochem Pharm 2012 83:6-15.
Serrano et al., Tannis: current knowledge of food sources, intake, bioavailability and biological effects, Mol Nutr Food Res 2009 53:S310-S329.
Shanmuganayagam et al., Differential effects of grape (Vitis vinifera) skin polyphenolics on human platelet aggregation and low-density lipoprotein oxidation, J Agric Food Chem 2012 60(23):5787-94.
Shrime et al., Flavonoid-rich cocoa consumption affects multiple cardiovascular risk factors in a meta-analysis of short-term studies, J Nutr 2011 141:1982-1988.
Soto et al., Antioxidant activity and consumer acceptance of grape seed flour-containing food products, International Journal of Food Science and Technology 2012 47:592-602.
Tamura, "Method for preparing fruit with enhanced GAMMA-aminobutyric acid having blood pressure lowering, tranquilizing, and obesity preventing effects," Database TCM [Online] 2008 (XP-002708065).
Vislocky and Fernandez, Biomedical effects of grape products, Nutri Rev 2010 68(1):656-670.
Weseler et al., Pleiotropic benefit of monomeric and oligomeric flavanols on vascular health—a randomized controlled clinical pilot study, Plos One 2011 6(12):e28460.
Written Opinion dated Jul. 6, 2015 for application No. PCT/US15/26825.
Yano et al., Improvements in the bread-making quality of gluten-free rice batter by glutathione, J Agric Food Chem 2010 58:7949-7954.
Yunoki et al., Effect of dietary wine pomace extract and oleanolic acid on plasma lipids in rats fed high-fat diet and its DNA microarray analysis, J Agric Food Chem 2008 56:12052-12058.
Zheng et al., Green tea intake lowers fasting serum total and LDL cholesterol in adults: a meta-analysis of 14 randomized controlled trials, Am J Clin Nutr 2011 94:601-10.
Hoye, Value-added product development utilizing Washington state grape seed flour, Doctoral dissertation, thesis submitted Washington State University, School of Food Science, 2009.
Shi et al., Optimization of the extraction of polyphenols from grape seed meal by aqueous ethanol solution, Journal of Food Agriculture & Environment, 2003, vol. 1(2) 42-27.
D'Alonzo, Scope and Impact of Allergic Rhinitis, Jun. 2002, S2-6, 102(6 Suppl 2).
Lutterodt et al., Fatty acid composition, oxidative stability, antioxidant and antiproliferative properties of selected cold-pressed grape seed oils and flours, Food Chemistry 2011 128(2):391-399.
Thiruchenduran et al., Protective effect of grape seed proanthocyanidins against cholesterol cholic acid diet-induced hypercholesterolemia in rats, Cardiovascular Pathology 2011 20(6):361-368.
Yamakoshi et al., Effect of proanthocyanidin-rich extract from grape seeds on human fecal flora and fecal odor, Microbial Ecology in Health and Disease 2011 13:25-31.
Yun Ju Woo et al. Grape seed proanthocyanidin extract ameliorates monosodium iodoacetate-induced osteoarthritis, 2011 Exp. Mol. Med vol. 43:10, p. 561-570.
Janisch et al., "Simulated Digestion of Vitis vinifera seed powder: Polyphenolic content and antioxidant properties", J. Agric. Food Chem. 2006, 54, p. 4839-4848.
Notice of Allowance dated Jun. 18, 2018 in U.S. Appl. No. 14/398,093.

* cited by examiner

Diet Composition

| WY51 | DRY WEIGHT BASIS | | | | | | | | | |
|---|---|---|---|---|---|---|---|---|---|---|
| | A | B | C | D | E | F | G | H | I | J |
| Ingredient | Control | ChrSd | CabSd | SyrSd | ChrSk | CabSk | SyrSk | ChrOil | SyrOil | GenOil |
| Fat 20% | | | | | | | | | | |
| Butter | 80.0 | 80.0 | 80.0 | 80.0 | 80.0 | 80.0 | 80.0 | 80.0 | 80.0 | 80.0 |
| Corn Oil-VitE | 100.0 | 67.3 | 70.5 | 71.3 | 73.5 | 71.2 | 71.6 | 0.0 | 0.0 | 0.0 |
| Fish | 20.0 | 20.0 | 20.0 | 20.0 | 20.0 | 20.0 | 20.0 | 20.0 | 20.0 | 20.0 |
| Cholesterol* | 1.0 | 1.0 | 1.0 | 1.0 | 1.0 | 1.0 | 1.0 | 1.0 | 1.0 | 1.0 |
| Grape oil | | | | | | | | 100.0 | 100.0 | 100.0 |
| Grape Skin | | | | | 100.0 | 100.0 | 100.0 | | | |
| Grape Seed | 0.0 | 100.0 | 100.0 | 100.0 | 0.0 | 0.0 | 0.0 | 0.0 | 0.0 | 0.0 |
| Fiber, 5% | | | | | | | | | | |
| Cellulose (.95 solids) | 52.5 | 52.5 | 52.5 | 52.5 | 17.6 | 20.9 | 25.0 | 52.5 | 52.5 | 52.5 |
| Protein 20% | | | | | | | | | | |
| Casein | 200.0 | 182.5 | 182.0 | 182.7 | 188.9 | 189.2 | 188.9 | 200.0 | 200.0 | 200.0 |
| Starch, Balance | | | | | | | | | | |
| Corn Starch | 495.5 | 445.6 | 443.0 | 441.5 | 468.0 | 466.7 | 462.4 | 495.5 | 495.5 | 495.5 |
| Other: | | | | | | | | | | |
| DL Methionine | 3.0 | 3.0 | 3.0 | 3.0 | 3.0 | 3.0 | 3.0 | 3.0 | 3.0 | 3.0 |
| Choline Bitartrate | 3.0 | 3.0 | 3.0 | 3.0 | 3.0 | 3.0 | 3.0 | 3.0 | 3.0 | 3.0 |
| Mineral Mix | 35.0 | 35.0 | 35.0 | 35.0 | 35.0 | 35.0 | 35.0 | 35.0 | 35.0 | 35.0 |
| Vitamin Mix - VitE | 10.0 | 10.0 | 10.0 | 10.0 | 10.0 | 10.0 | 10.0 | 10.0 | 10.0 | 10.0 |
| TOTAL WT | 1000.0 | 1000.0 | 1000.0 | 1000.0 | 1000.0 | 1000.0 | 1000.0 | 1000.0 | 1000.0 | 1000.0 |
| Calories/kg | 4582 | 4461.4 | 4464.8 | 4463.3 | 4588.2 | 4553.2 | 4528.7 | 4582.0 | 4582.0 | 4582.0 |

FIGURE 2

| Gene | Avg | StdDev |
|---|---|---|
| ADPN | 0.94 | 0.33 |
| LEPTIN | 0.62 | 0.24 |
| TNFα | 0.84 | 0.24 |
| MCP-1 | 0.89 | 0.22 |
| CD68 | 0.98 | 0.35 |
| LBP | 0.8 | 0.23 |
| MMP-9 | 2.28 | 2.52 |
| RAPTOR | 0.95 | 0.26 |
| PPARγ2 | 0.57 | 0.13 |

FIGURE 16

| Gene | Avg | StdDev |
| --- | --- | --- |
| SCD1 | 0.21 | 0.28 |
| FAS | 1.69 | 0.98 |
| SREBP-1c | 0.63 | 0.28 |
| ACOX1 | 2.42 | 0.37 |
| PPARα | 1.36 | 0.16 |
| | | |
| SREBP-2 | 1.63 | 0.47 |
| HMG-CoAR | 1.55 | 0.39 |
| CYP51 | 6.58 | 3.2 |
| LDLR | 1.46 | 0.66 |
| ABCG5 | 0.24 | 0.09 |
| | | |
| CYP7a1 | 4.86 | 3.3 |
| ABCB11 | 1.32 | 0.33 |
| | | |
| RAPTOR | 1.38 | 0.24 |
| DGAT2 | 0.88 | 0.21 |
| AKT2 | 1.06 | 0.21 |

FIGURE 17

SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: synthetic primer

<400> SEQUENCE: 1
agcagtaggg aatcttcca                                              19

<210> SEQ ID NO 2
<211> LENGTH: 17
<212> TYPE: DNA
<213> ORGANISM: Artificial Sequence
<220> FEATURE:
<223> OTHER INFORMATION: synthetic primer

<400> SEQUENCE: 2
caccgctaca catggag                                                17

<210> SEQ ID NO 3
<211> LENGTH: 17
<212> TYPE: DNA
<213> ORGANISM: Artificial Sequence
<220> FEATURE:
<223> OTHER INFORMATION: synthetic primer

<400> SEQUENCE: 3
ctcctggaaa cgggtgg                                                  17

<210> SEQ ID NO 4
<211> LENGTH: 22
<212> TYPE: DNA
<213> ORGANISM: Artificial Sequence
<220> FEATURE:
<223> OTHER INFORMATION: Synthetic primer

<400> SEQUENCE: 4
ggtgttcttc ccgatatcta ca                                            22

<210> SEQ ID NO 5
<211> LENGTH: 24
<212> TYPE: DNA
<213> ORGANISM: Artificial Sequence
<220> FEATURE:
<223> OTHER INFORMATION: synthetic primer

<400> SEQUENCE: 5
cccttattgt tagttgccat catt                                          24

<210> SEQ ID NO 6
<211> LENGTH: 21
<212> TYPE: DNA
<213> ORGANISM: Artificial Sequence
<220> FEATURE:
<223> OTHER INFORMATION: synthetic primer

<400> SEQUENCE: 6
actcgttgta cttcccattg t                                             21

<210> SEQ ID NO 7
<211> LENGTH: 16
<212> TYPE: DNA
<213> ORGANISM: Artificial Sequence
<220> FEATURE:
<223> OTHER INFORMATION: synthetic primer

<400> SEQUENCE: 7
gcacaagcag tggagt                                                   16

<210> SEQ ID NO 8
<211> LENGTH: 15
<212> TYPE: DNA
<213> ORGANISM: Artificial Sequence
<220> FEATURE:
<223> OTHER INFORMATION: synthetic primer

<400> SEQUENCE: 8
agtsctcttg ggtag                                                    15

<210> SEQ ID NO 9
<211> LENGTH: 20
<212> TYPE: DNA
<213> ORGANISM: Artificial Sequence
<220> FEATURE:
<223> OTHER INFORMATION: synthetic primer

```
<400> SEQUENCE: 9
caagccctac aagaaatccg                                               20

<210> SEQ ID NO 10
<211> LENGTH: 18
<212> TYPE: DNA
<213> ORGANISM: Artificial Sequence
<220> FEATURE:
<223> OTHER INFORMATION: synthetic primer

<400> SEQUENCE: 10
tccaccgaac cgaagttg                                                 18

<210> SEQ ID NO 11
<211> LENGTH: 21
<212> TYPE: DNA
<213> ORGANISM: Artificial Sequence
<220> FEATURE:
<223> OTHER INFORMATION: synthetic primer

<400> SEQUENCE: 11
gcgattgatg gtgatacggt t                                             21

<210> SEQ ID NO 12
<211> LENGTH: 24
<212> TYPE: DNA
<213> ORGANISM: Artificial Sequence
<220> FEATURE:
<223> OTHER INFORMATION: synthetic primer

<400> SEQUENCE: 12
agccaagcct tgacgaacta aagc                                          24

<210> SEQ ID NO 13
<211> LENGTH: 19
<212> TYPE: DNA
<213> ORGANISM: Artificial Sequence
<220> FEATURE:
<223> OTHER INFORMATION: synthetic primer

<400> SEQUENCE: 13
tcctacggga ggcagcagt                                                19

<210> SEQ ID NO 14
<211> LENGTH: 26
<212> TYPE: DNA
<213> ORGANISM: Artificial Sequence
<220> FEATURE:
<223> OTHER INFORMATION: synthetic primer

<400> SEQUENCE: 14
ggactaccag ggtatctaat cctgtt                                        26
```

THERAPEUTIC USE OF CHARDONNAY SEED PRODUCTS

1. BACKGROUND

1.1. Metabolic Conditions

Obesity is a well-known risk factor for the development of many very common diseases such as atherosclerosis, hypertension, type 2 diabetes (non-insulin dependent diabetes mellitus (NIDDM)), dyslipidemia, coronary heart disease, and osteoarthritis and various malignancies. It also causes considerable problems through reduced motility and decreased quality of life. The incidence of obesity and thereby also these diseases is increasing throughout the entire industrialized world.

The term obesity implies an excess of adipose tissue. In this context obesity is best viewed as any degree of excess adiposity that imparts a health risk. The cut off between normal and obese individuals can only be approximated, but the health risk imparted by the obesity is probably a continuum with increasing adiposity.

Even mild obesity increases the risk for premature death and conditions such as diabetes, dyslipidemia, hypertension, atherosclerosis, gallbladder disease and certain types of cancer. In the industrialized western world the prevalence of obesity has increased significantly in the past few decades. Because of the high prevalence of obesity and its health consequences, its prevention and treatment should be a high public health priority.

When energy intake exceeds expenditure, the excess calories are stored predominately in adipose tissue, and if this net positive balance is prolonged, obesity results, i.e., there are two components to weight balance, and an abnormality on either side (intake or expenditure) can lead to obesity. This process may be counteracted by increasing the energy expenditure (for instance via exercise) or decreasing the energy intake (for instance by dieting). Except for exercise, diet and food restriction, which is not feasible for a vast number of subjects, no convincing treatment for reducing body weight effectively and acceptably currently exist.

One possible way to increase energy expenditure is by increasing the metabolic rate. Agents which act by increasing the metabolic rate may thus be useful for treating obesity, but also for treating other conditions such as atherosclerosis, hypertension, diabetes, especially type 2 diabetes (NIDDM (non-insulin dependent diabetes mellitus)), dyslipidemia, coronary heart disease, gallbladder disease, osteoarthritis and various types of cancer such as endometrial, breast, prostate and colon cancers and the risk for premature death.

Thus, it would be desirable to identify agents that can increase energy expenditure. Preferably, such agents would be natural agents that avoid side effects associated with pharmaceutical compounds.

1.2. Gut Biome

The infant gut is sterile before birth. After birth, the gut is rapidly colonized by environmental bacteria until a dense gut biome is established. Infants delivered vaginally acquire gut colonizing bacteria from their mother's vaginal and fecal flora. In contrast, infants delivered by cesarean section are not exposed to their mother's vaginal and fecal flora during birth and thus develop a gut biome that is different in composition than the gut biome of infants delivered vaginally. These differences in gut biome composition persist in the months immediately following birth. Likewise, differences in gut biome composition have been observed between infants that are breast fed and those that are formula fed.

The adult human gut has approximately $10^{13}$ (10,000,000,000,000) individual residents (Bäckhead, F., et al. (2004) *PNAS* Volume 101; no 44 pp. 15718-15723) and there are three consistent enterotypes established across many human cultural backgrounds (Arumugam, M. et al. (2011) *Nature* Vol. 473 pp. 174-180). The gut biome is influenced by plant based polyphenols in the diet and it is believed that the microbes convert them to be bioavailable to the human host (Rastmanesh, R. (2011), *Chemico-Biol. Interact*. Vol. 189 pp. 1-8; Moco, S., F. J. Martin, and S. Rezzi. (2012) *J. Proteome Res*. Volume 11, pp. 4781-4790). Acting as an organ, the gut biome is also responsible for conversion and production of key vitamins such as cholecalciferol (vitamin $D_{25}$), biotin (vitamin H), riboflavin (vitamin $B_2$), pantothenate (vitamin $B_5$), ascorbate (vitamin C), thiamine (vitamin $B_1$) and folate (vitamin $B_9$); particularly in two (*Bacteroides* and *Prevotella*) of the three enterotypes (*Bacteroides*, Ruminococcus, and *Prevotella*) discovered. Some polyphenols have been described as vitamins in their own right by Dr. Norman Hollenberg, Professor of Medicine at Harvard Medical School. However, modern diets, particularly Western diets comprising high amounts of processed foods, may promote a gut biome composition that fails to convert or produce adequate or optimal amounts of these key vitamins.

Thus, it would be desirable to identify agents that can "fill in the nutritional gaps" caused by consumption of traditionally processed foods and modulate the human gut biome to achieve improved health. Preferably, such agents would be natural agents that avoid side effects associated with pharmaceutical compounds.

2. SUMMARY

The present disclosure relates to health benefits of Chardonnay seed products.

In certain aspects, the present disclosure relates to a method of increasing lipid metabolism in a mammal by administering an amount of Chardonnay seed product that is effective to increase lipid metabolism in the mammal.

In certain aspects, the present disclosure relates to a method of increasing a mammal's metabolic rate by administering an amount of Chardonnay seed product that is effective to increase the mammal's metabolic rate.

The present disclosure also relates a method of treating or preventing obesity, a cardiovascular disease, a dyslipidemia, a dyslipoproteinemia or a glucose metabolism disorder in a mammal by administering to a mammal an amount of Chardonnay seed product that is effective to treat or prevent obesity in the mammal.

The present disclosure further relates to a method of treating or preventing a cardiovascular disease in a mammal by administering to a mammal an amount of Chardonnay seed product that is effective to treat or prevent said cardiovascular disease in the mammal. In certain aspects, the cardiovascular disease is arteriosclerosis, atherosclerosis, stroke, ischemia, endothelium dysfunctions, peripheral vascular disease, coronary heart disease, myocardial infarcation, cerebral infarction or restenosis.

The present disclosure further relates to a method of treating or preventing a dyslipidemia in a mammal by administering to a mammal an amount of Chardonnay seed product effective to treat or prevent said dyslipidemia in the mammal. In certain aspects, the dyslipidemia is hyperlipidemia or low blood levels of high density lipoprotein (HDL)

cholesterol. In certain aspects, the hyperlipidemia is familial hypercholesterolemia, familial combined hyperlipidemia, reduced or deficient lipoprotein lipase levels or activity, hypertriglyceridemia, hypercholesterolemia, high blood levels of ketone bodies, high blood levels of Lp(a) cholesterol, high blood levels of low density lipoprotein (LDL) cholesterol, high blood levels of very low density lipoprotein (VLDL) cholesterol, or high blood levels of non-esterified fatty acids.

The present disclosure further relates to a method of treating or preventing a dyslipoproteinemia in a mammal by administering an amount of Chardonnay seed product effective to treat or prevent said dyslipoproteinemia. In certain aspects, the dyslipoproteinemia is high blood levels of LDL, high blood levels of apolipoprotein B (apo B), high blood levels of Lp(a), high blood levels of apo(a), high blood levels of VLDL, low blood levels of HDL, reduced or deficient lipoprotein lipase levels or activity, hypoalphalipoproteinemia, lipoprotein abnormalities associated with diabetes, lipoprotein abnormalities associated with obesity, lipoprotein abnormalities associated with Alzheimer's Disease, or familial combined hyperlipidemia.

The present disclosure further relates to a method of treating or preventing a glucose metabolism disorder in a mammal by administering to a mammal an amount of Chardonnay seed product effective to treat or prevent said glucose metabolism disorder in the mammal. In certain aspects, the glucose metabolism disorder is impaired glucose tolerance, insulin resistance, insulin resistance related breast, colon or prostate cancer, diabetes, pancreatitis, hypertension, polycystic ovarian disease, high levels of blood insulin, or high levels of blood glucose. In certain aspects, the diabetes is non-insulin dependent diabetes mellitus (NIDDM), insulin dependent diabetes mellitus (IDDM), gestational diabetes mellitus (GDM), or maturity onset diabetes of the young (MODY).

The disclosure further relates to a method of treating or preventing metabolic syndrome in a mammal by administering to a mammal an amount of Chardonnay seed product effective to treat or prevent metabolic syndrome in the mammal.

In certain aspects, an amount is administered that is effective to modulate expression of one or more genes involved in fat, cholesterol, and/or bile metabolism. In specific embodiments, the amount is effective to increase expression of ACOX1 in hepatic tissue, to increase expression of CYP51 in hepatic tissue, to increase expression of CYP7a1 in hepatic tissue, to decrease expression of SCD1 in hepatic tissue, and/or to decrease expression of ABCG5 in hepatic tissue, for example by at least 10%, at least 20%, at least 50%, or at least 100%.

The present disclosure further relates to a method of increasing the amount of *Clostridium* bacteria in the gut of a mammal by administering to the mammal an amount of Chardonnay seed product effective to increase the amount of *Clostridium* bacteria in the gut of the mammal.

The present disclosure further relates to a method of decreasing the amount of Enterobacteriaceae bacteria in the gut of a mammal by administering to the mammal an amount of Chardonnay seed product effective to decrease the amount of Enterobacteriaceae bacteria in the gut of the mammal.

The present disclosure further relates to a method of increasing the amount of *Bacteroides fragilis* group bacteria in the gut of a mammal by administering to the mammal an amount of Chardonnay seed product effective to increase the amount of *Bacteroides fragilis* group bacteria in the gut of the mammal.

The present disclosure further relates to a method of treating or preventing lactic acidosis in a mammal by administering to the mammal an amount of Chardonnay seed product effective to treat or prevent lactic acidosis.

In certain embodiments of the methods, a second grape seed or grape skin product which is not a Chardonnay seed product is administered to the mammal. In certain aspects, the combination of Chardonnay seed product and second grape seed or grape skin product provides a therapeutic effect or health benefit which is greater than the effect of administration of Chardonnay seed product alone.

In certain aspects, the Chardonnay seed product is prepared from seeds having an epicatechin content of at least 600 mg of epicatechin per 100 g of seeds or an epicatechin content of at least 700 mg of epicatechin per 100 g of seeds. In specific embodiments, the epicatechin content ranges from 600-800 mg/100 g of seeds or from 650-800 mg/100 g of seeds.

In certain embodiments, the Chardonnay seed product is incorporated into a food or beverage product.

In certain embodiments, the Chardonnay seed product is Chardonnay seed flour. In certain embodiments, the Chardonnay seed product is Chardonnay seed extract. In certain embodiments, the Chardonnay seed product is from grapes grown in a Winkler region climate type I, II, III or IV.

In certain embodiments, the mammal is a domestic pet, e.g., a cat or a dog. In other embodiments of the methods, the mammal is a human. In other embodiments, the human is an infant.

The present disclosure further relates to an infant formula comprising a Chardonnay seed product and methods of using the infant formula to promote gut microbiome development in an infant. In certain aspects, the infant formula promotes gut microbiota development when administered to an infant by modulating levels of gut bacteria. In certain embodiments, the infant was delivered by cesarean section. In certain embodiments, the infant is formula fed.

3. BRIEF DESCRIPTION OF THE FIGURES

FIG. 1: Protein, fat, ash, carbohydrate, and total dietary fiber content of Chardonnay (Chr), Cabernet (Cab), and Syrah (Syr) seeds (Sd) and skins (Sk).

FIG. 2: Dietary composition of hamsters in Example 1.

Figure 3:
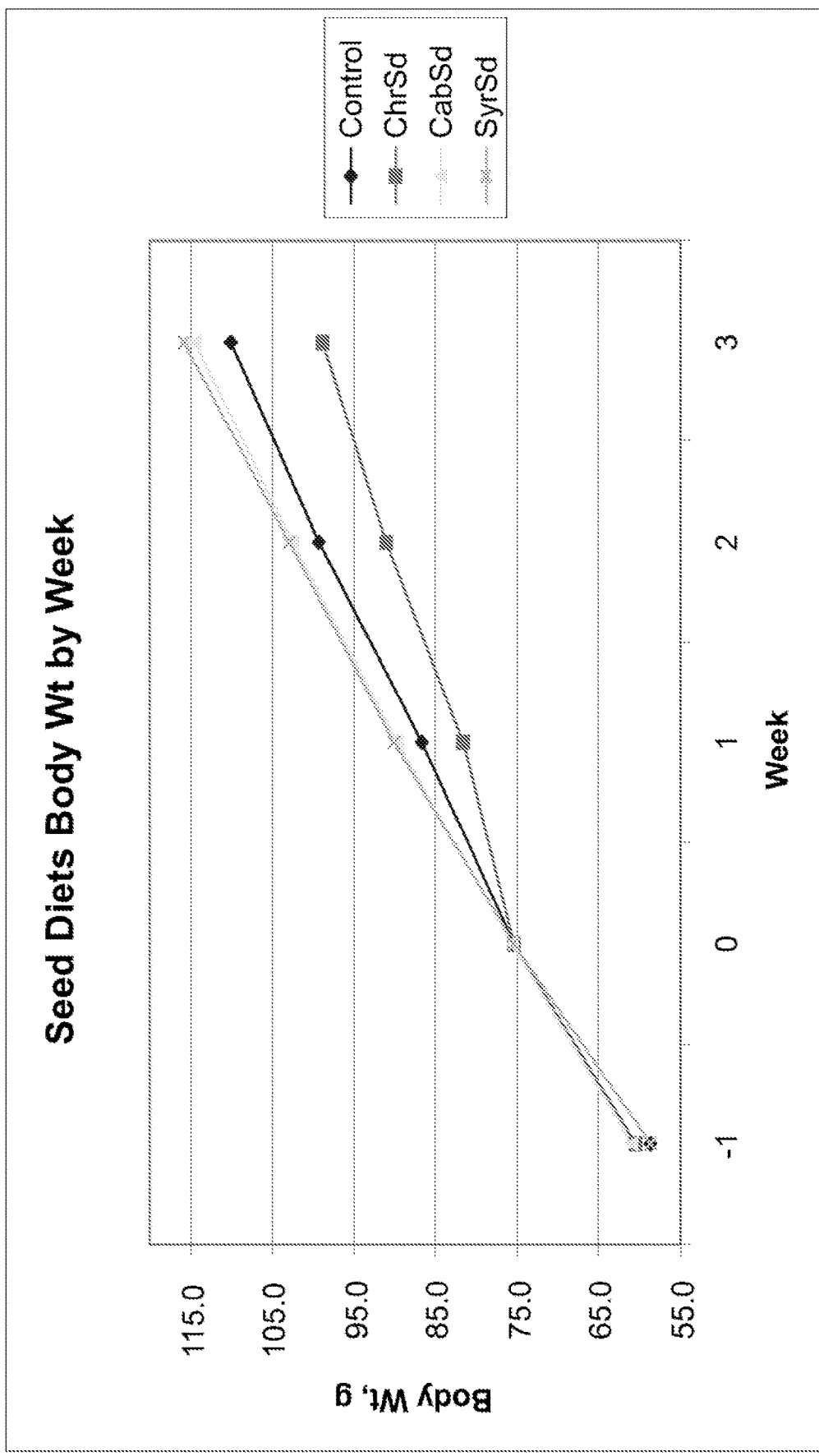

FIG. 3: Seed diets body weight by week of the animals of Example 1.

Figure 4:
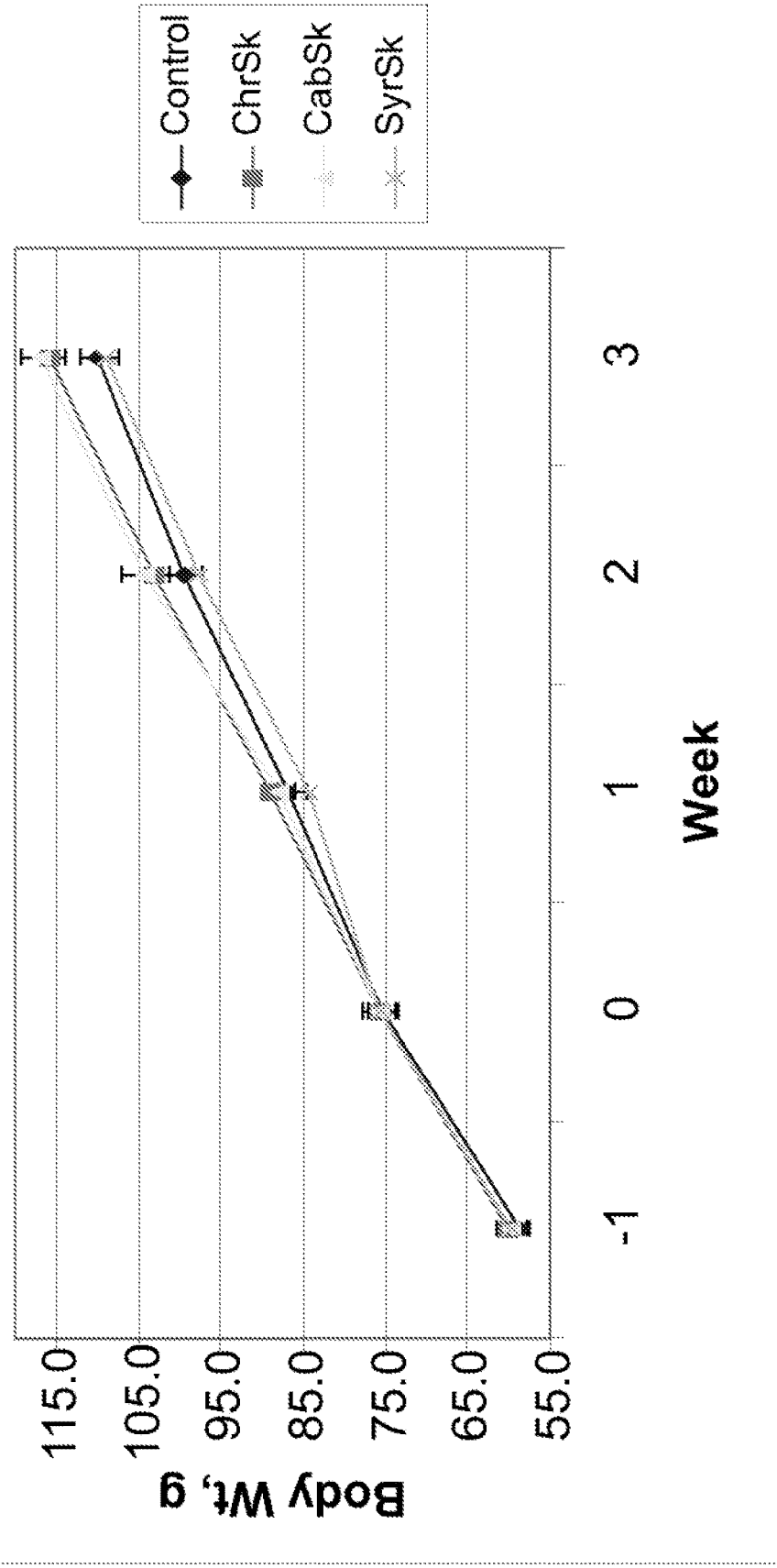

FIG. 4: Skin diets body weight by week of the animals of Example 1.

Figure 5:
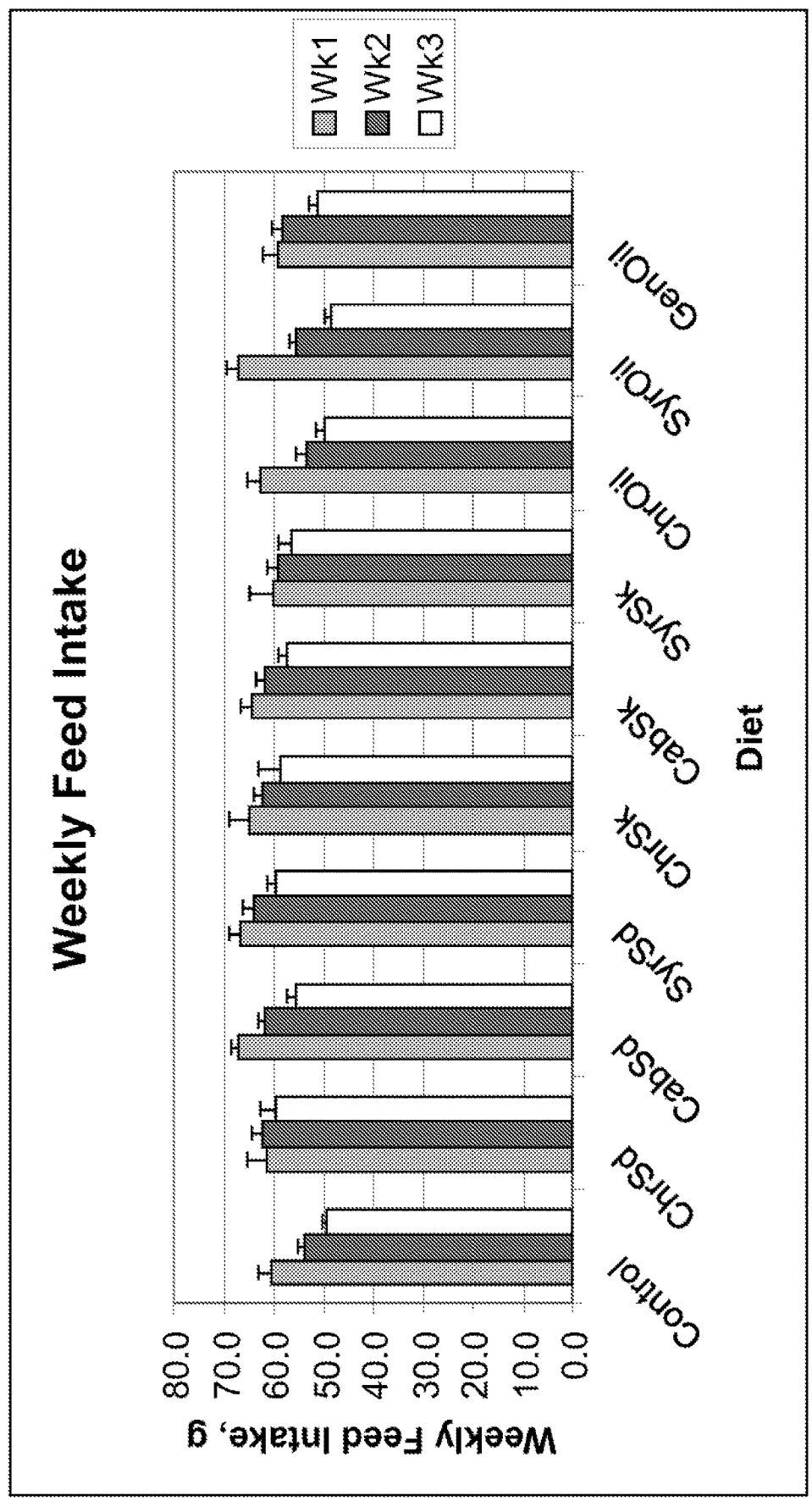

FIG. 5: Weekly feed intake of the animals of Example 1.

Figure 6:
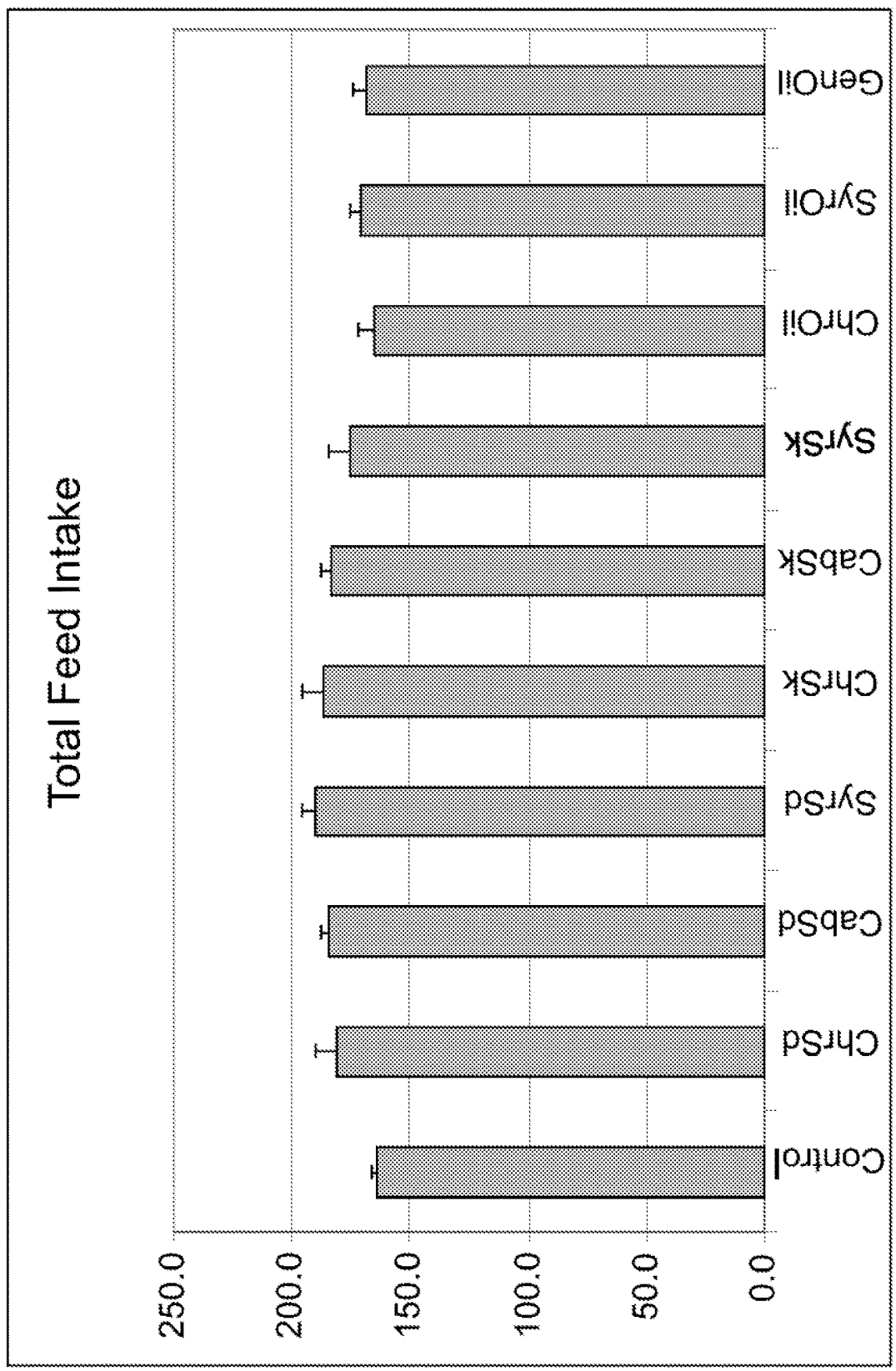

FIG. 6: Total feed intake of the animals of Example 1.

Figure 7:
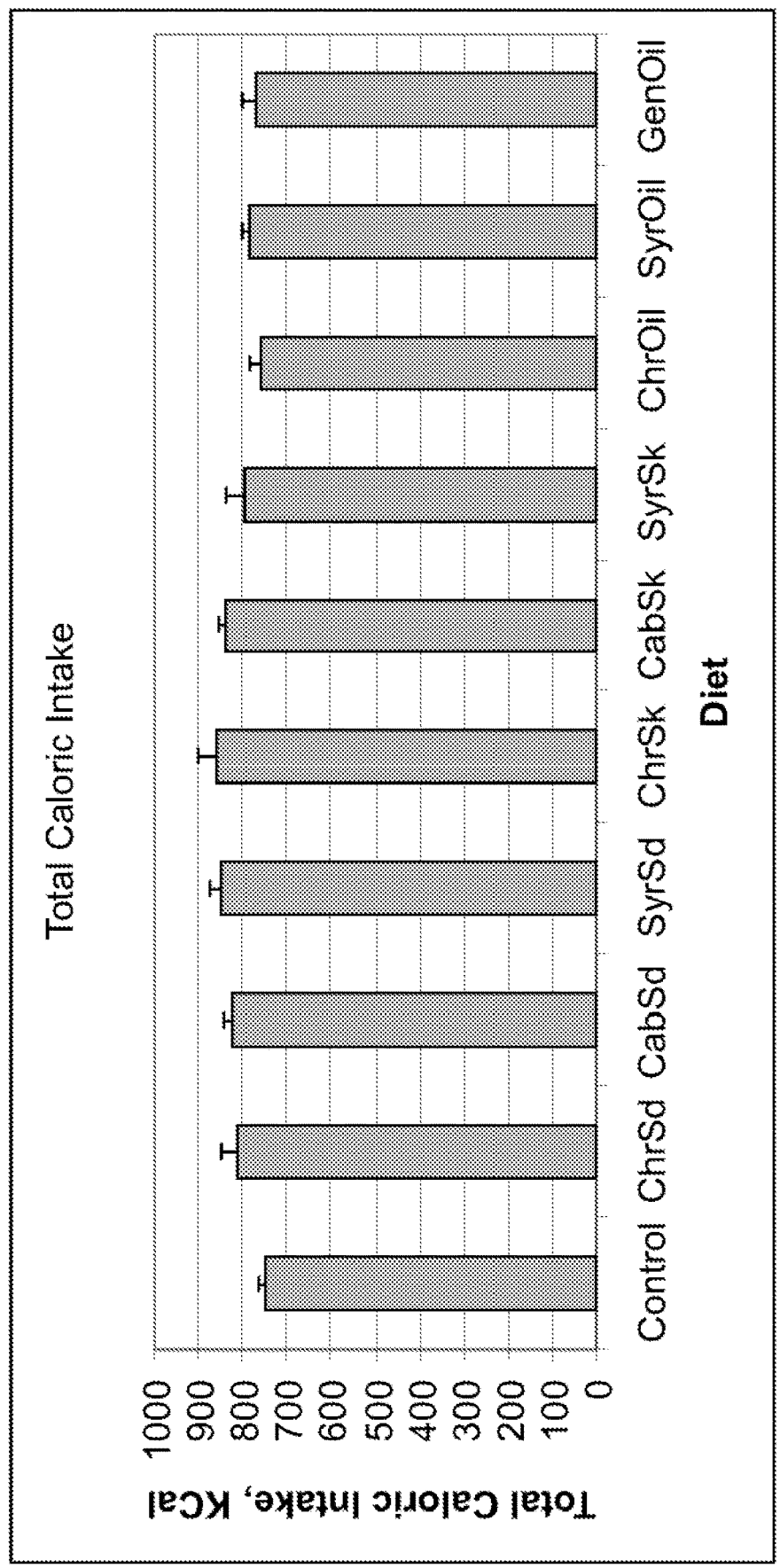

FIG. 7: Total caloric intake of the animals of Example 1.

Figure 8:
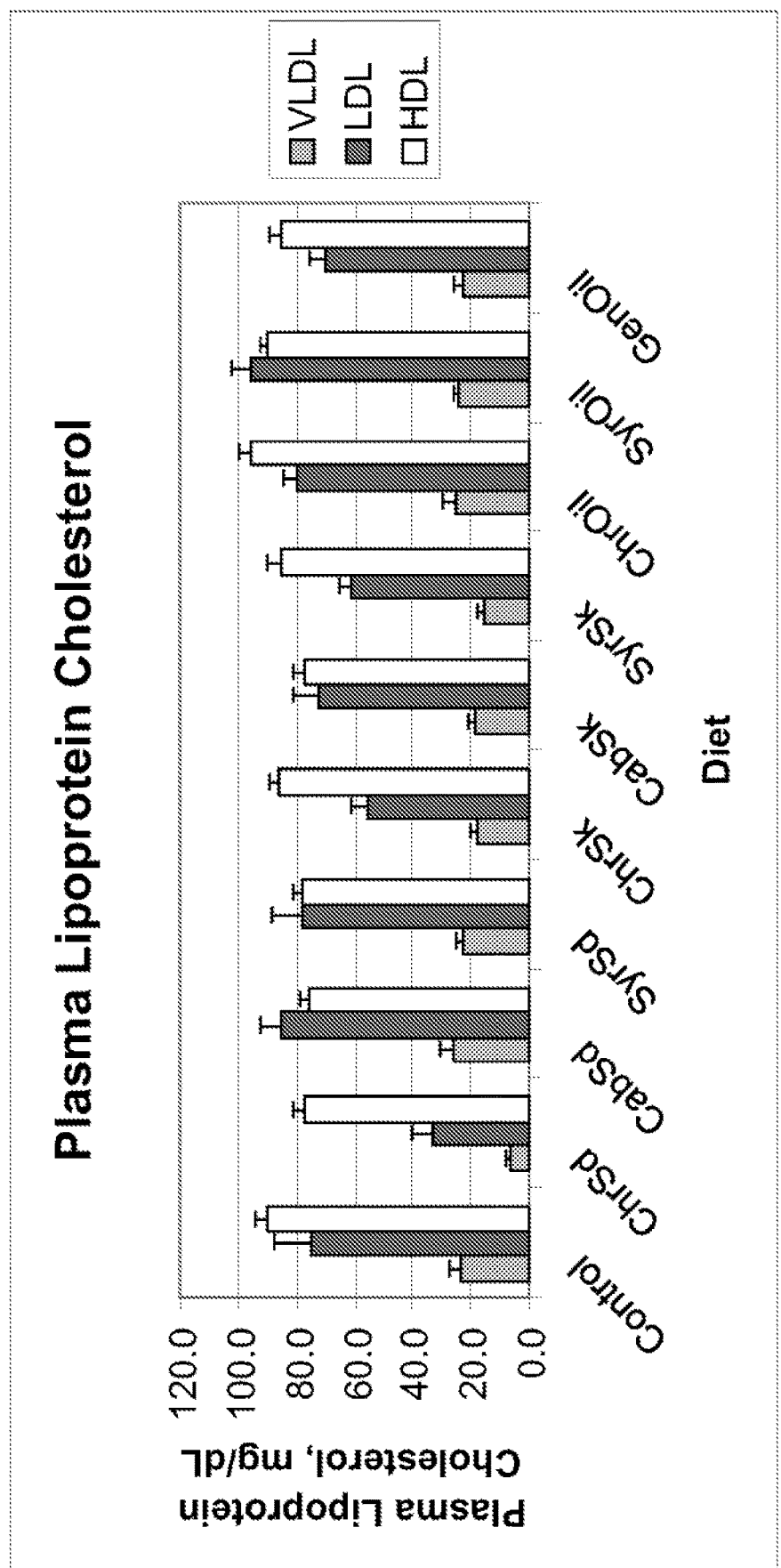

FIG. 8: Plasma lipoprotein cholesterol levels of the animals of Example 1 at the end of four weeks.

Figure 9:
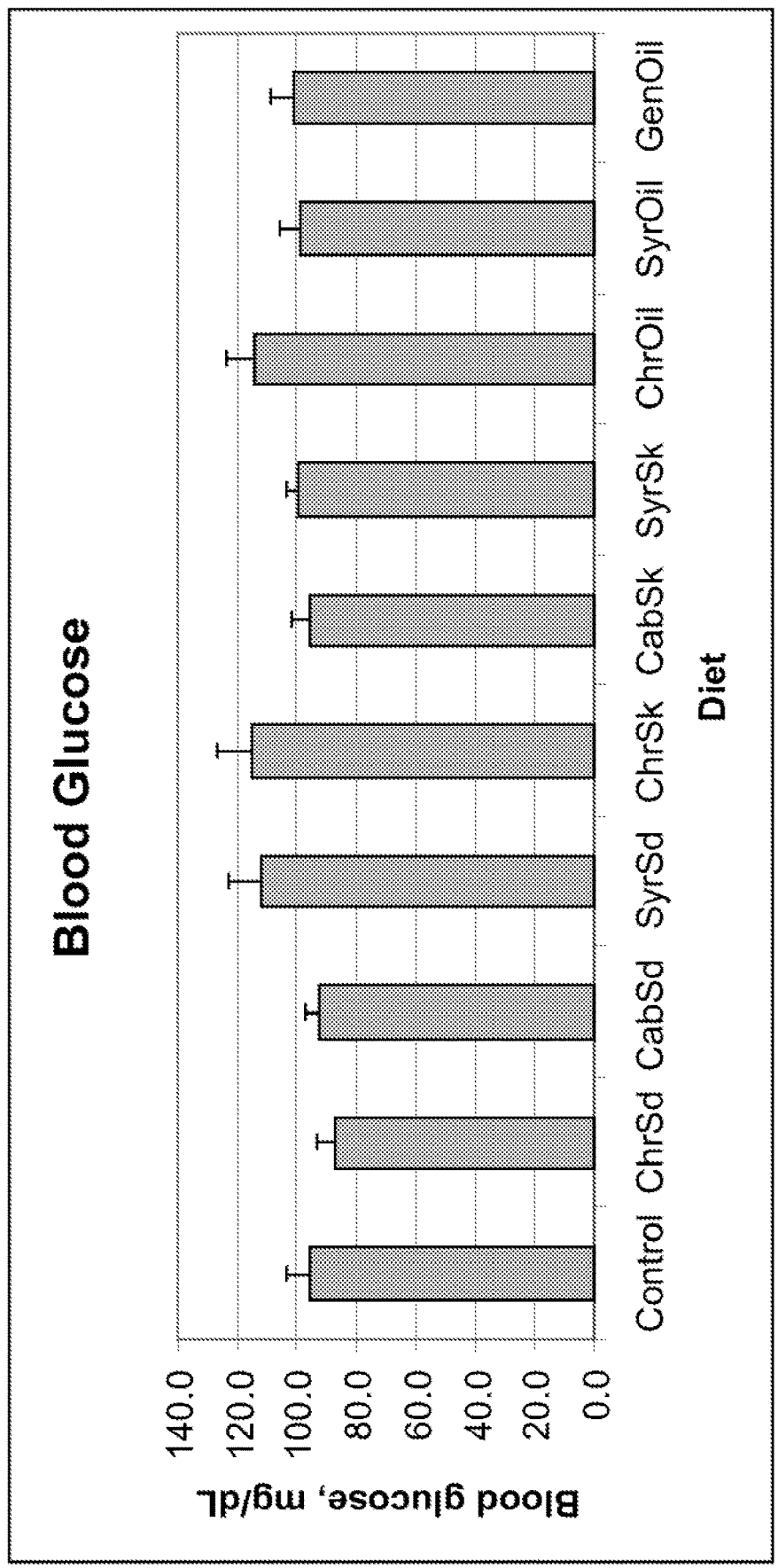

FIG. 9: Blood glucose levels of the animals of Example 1 at the end of four weeks.

Figure 10:
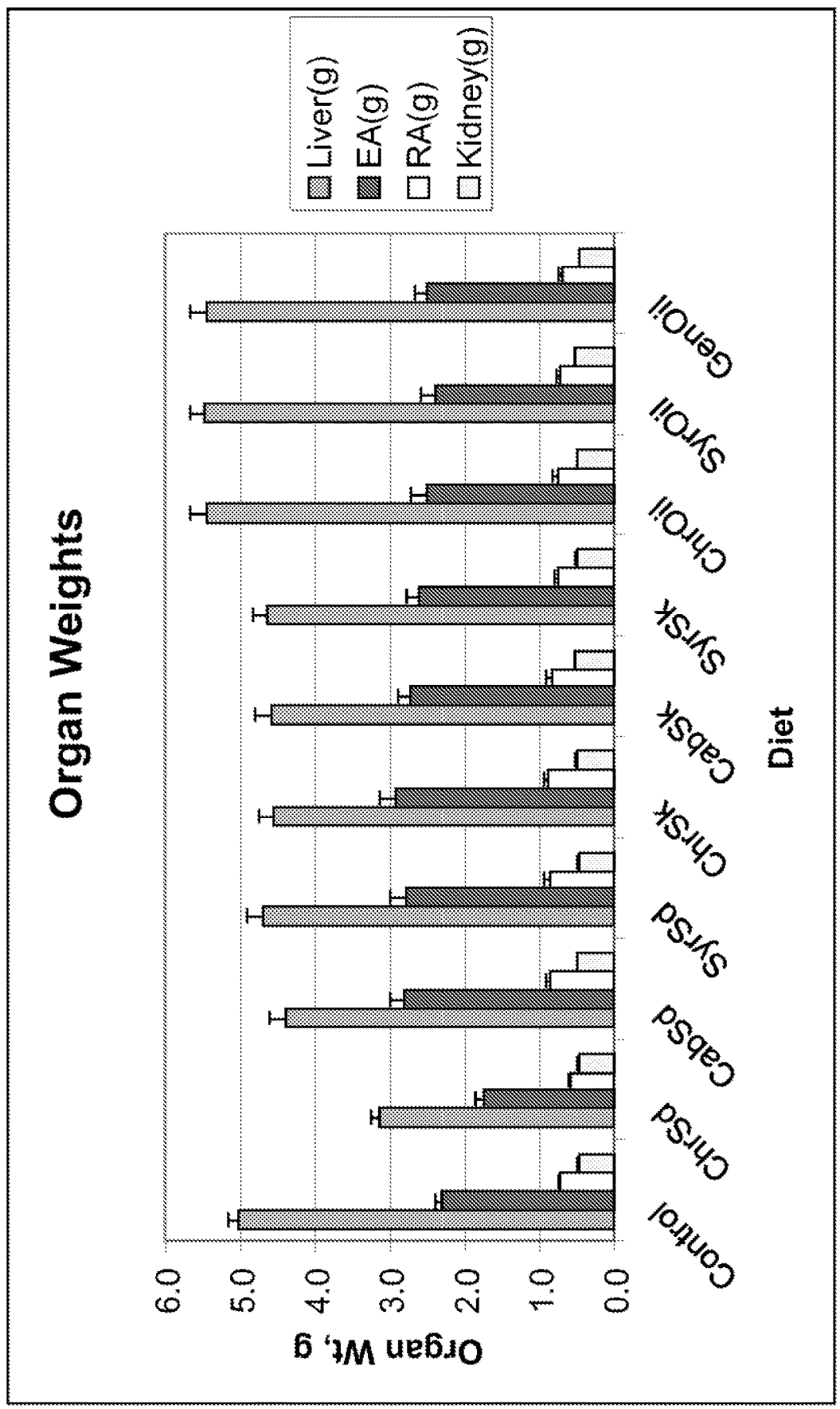

FIG. 10: Organ weights of the animals of Example 1 at the end of four weeks.

Figure 11:
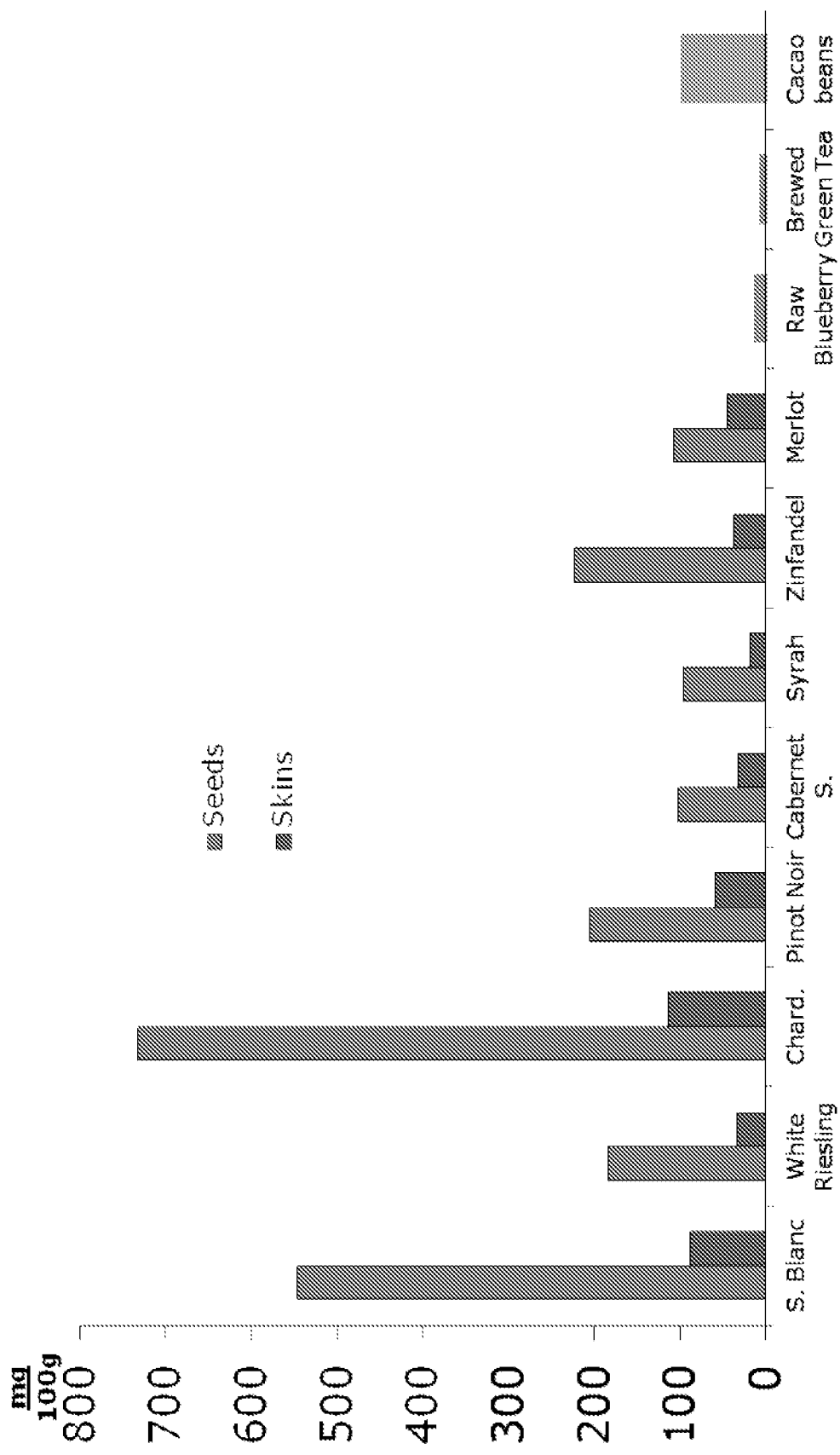

FIG. 11: Epicatechin levels in the seed and skin of different grape varieties.

Figure 12:
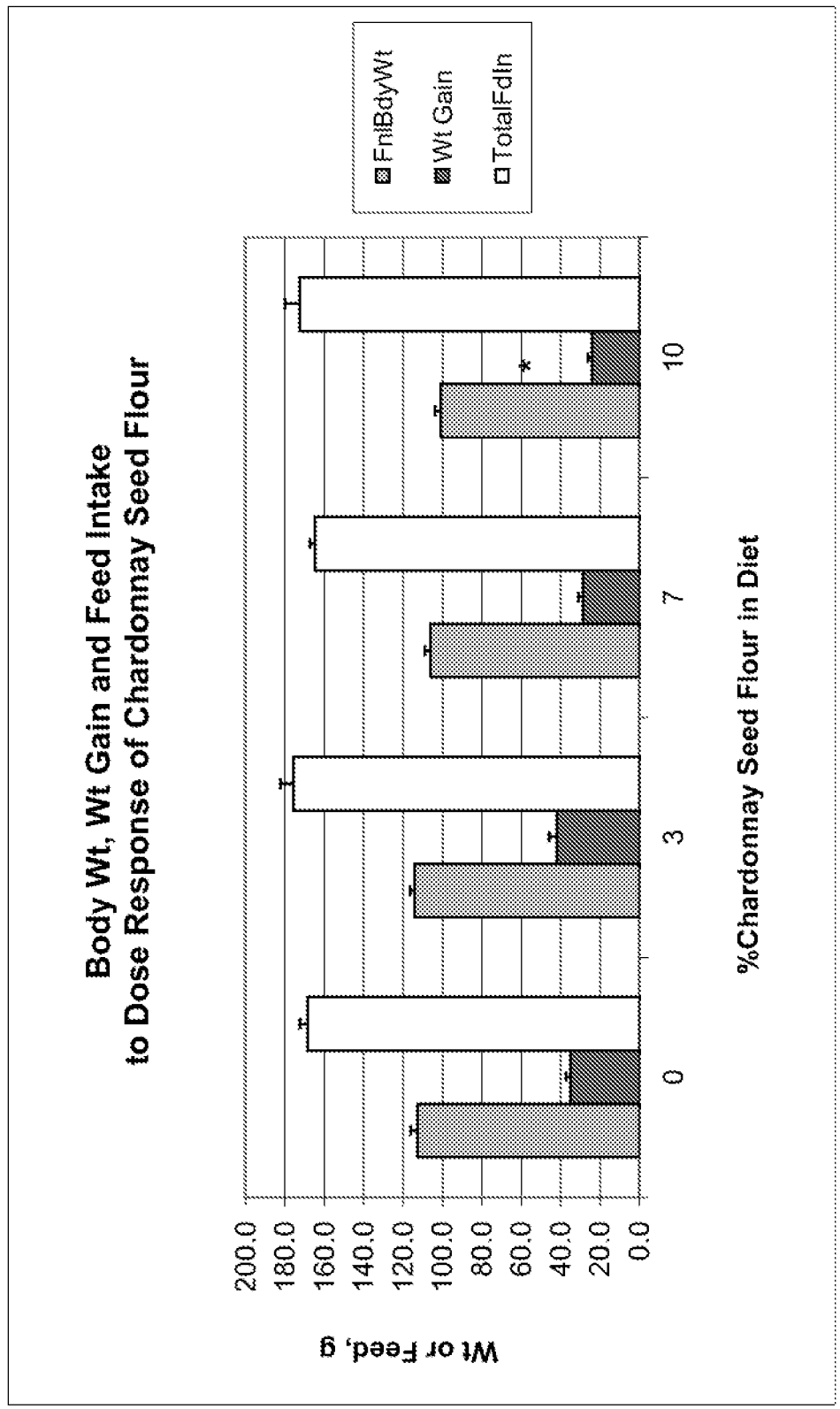

FIG. 12: Body weight, weight gain, and total feed intake of animals of Example 2 fed diets comprising 3%, 7%, and 10% Chardonnay seed flour by weight.

Figure 13:
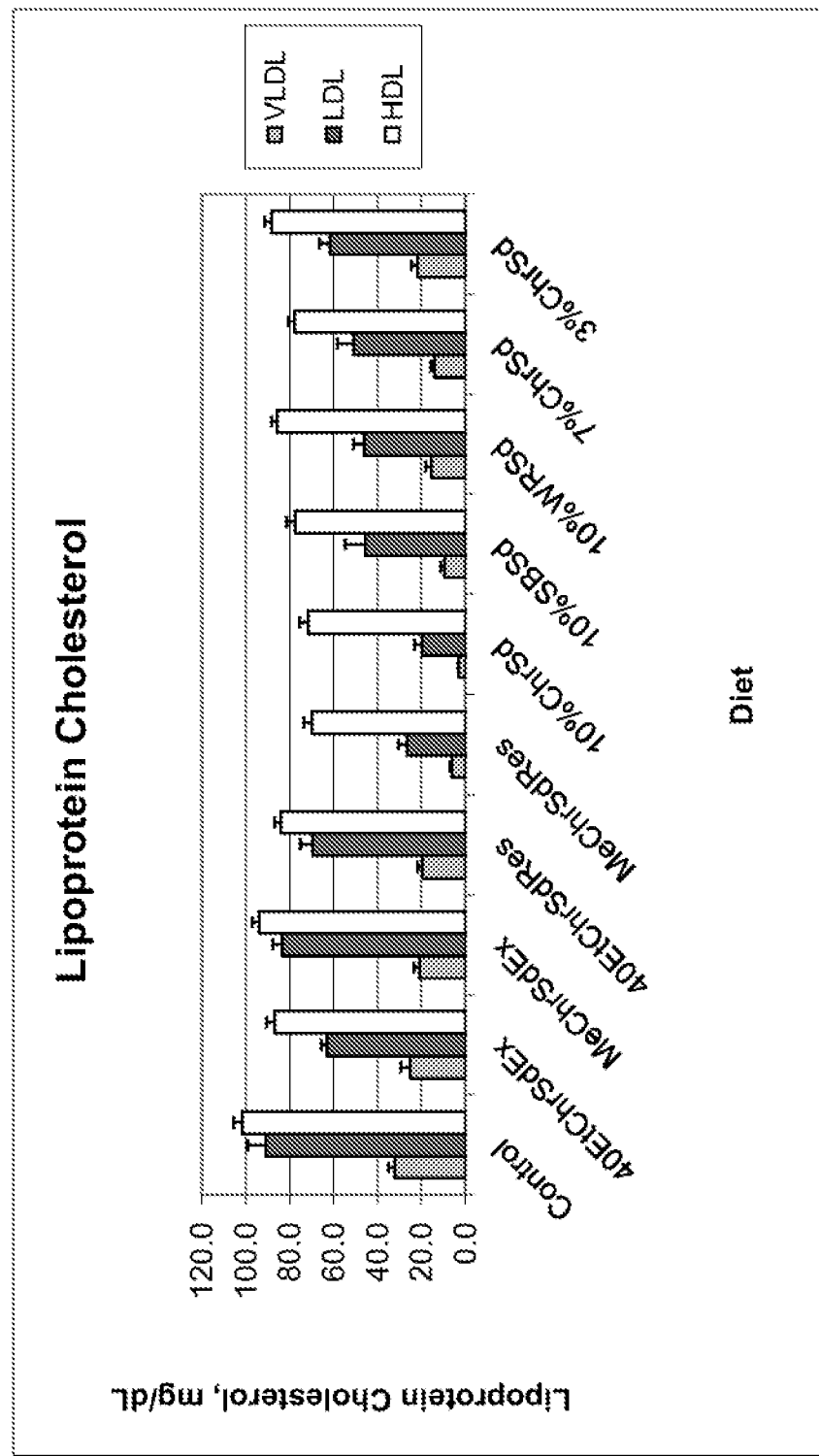

FIG. 13: VLDL, LDL, and HDL cholesterol levels of animals of Example 2 fed Chardonnay seed ethanol extract (40EtChrSdEx), Chardonnay seed methanol extract (MeChrSdEx), Chardonnay seed ethanol extract residue (40EtChrSdRes), Chardonnay seed methanol extract residue (MeChrSdRes), Chardonnay seed flour at 10%, 7%, and 3% by diet weight (10% ChrSd, 7% ChrSd, and 3% ChrSd, respectively), 10% White Riesling seed flour by diet weight (10% WRSd), and 10% Sauvignon Blanc seed flour by diet weight (10% SBSd) at the end of four weeks.

Figure 14:
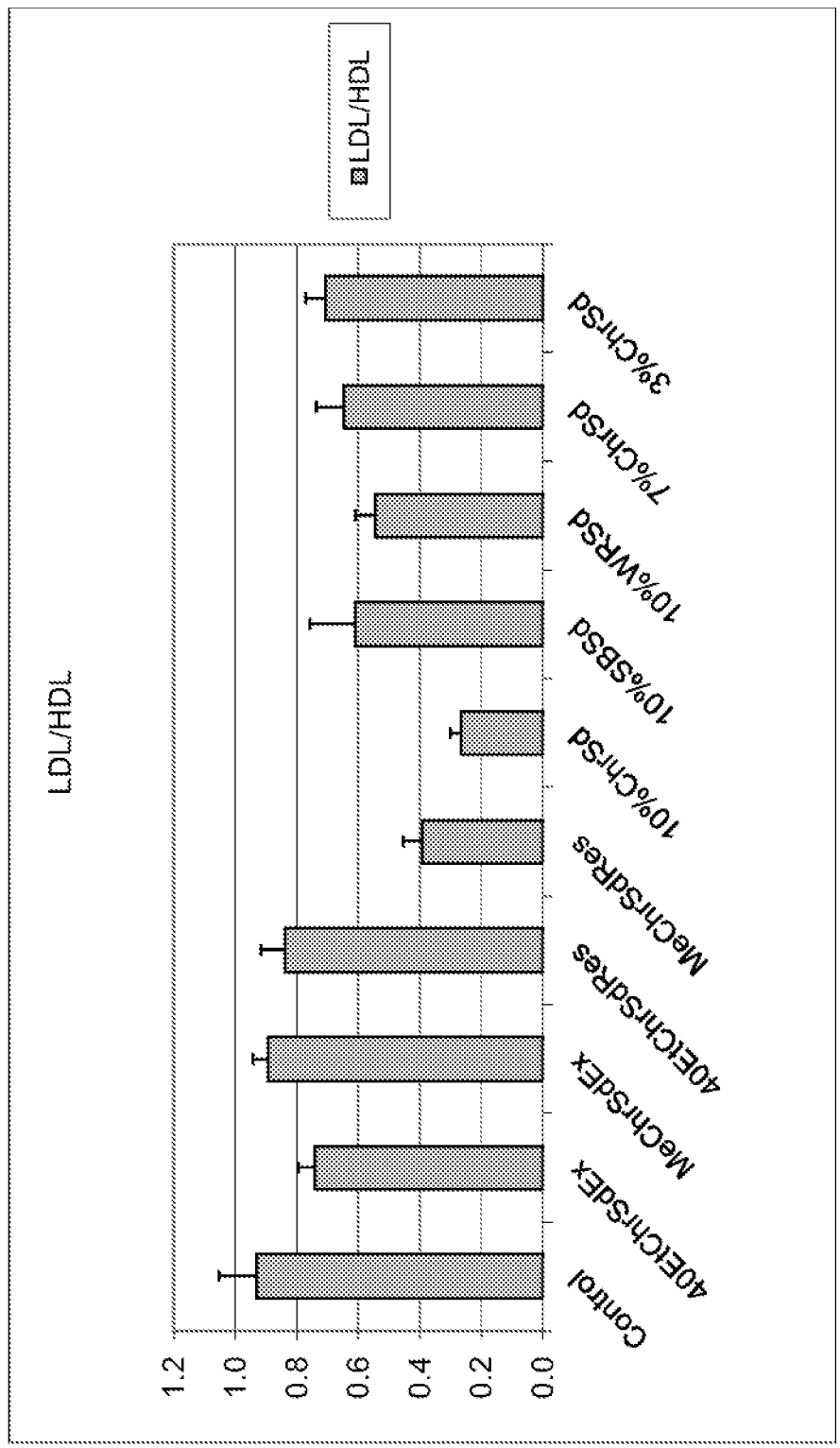

FIG. 14: LDL/HDL cholesterol ratio of animals of Example 2 fed Chardonnay seed ethanol extract (40EtChrSdEx), Chardonnay seed methanol extract (MeChrSdEx), Chardonnay seed ethanol extract residue (40EtChrSdRes), Chardonnay seed methanol extract residue (MeChrSdRes), Chardonnay seed flour at 10%, 7%, and 3% by diet weight (10% ChrSd, 7% ChrSd, and 3% ChrSd, respectively), 10% White Riesling seed flour by diet weight (10% WRSd), and 10% Sauvignon Blanc seed flour by diet weight (10% SBSd) at the end of four weeks.

Figure 15:
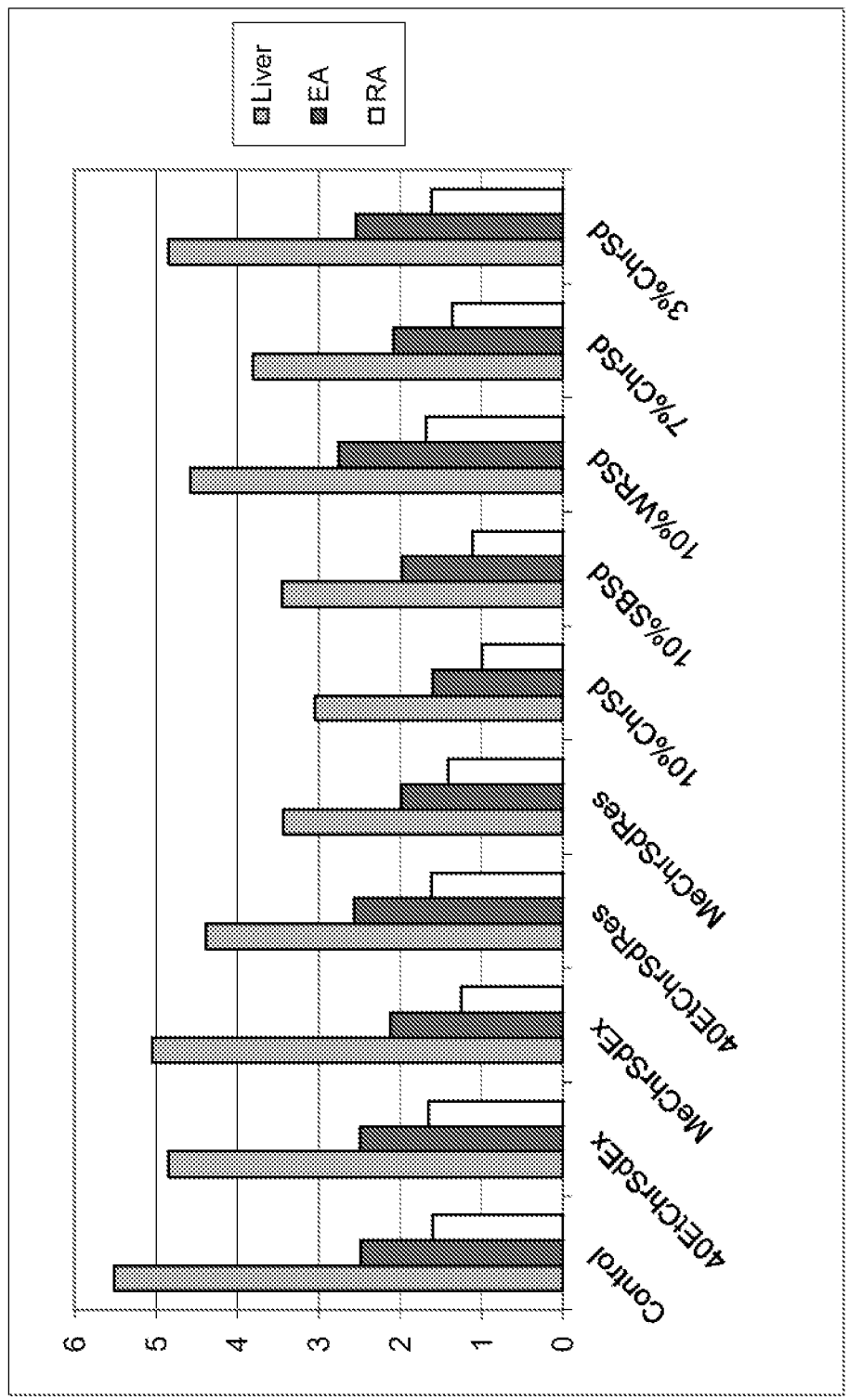

FIG. 15: Liver, Epidydimal Adipose (EA), and Retroperitoneal Adipose (RA) weights of animals of Example 2 fed Chardonnay seed ethanol extract (40EtChrSdEx), Chardonnay seed methanol extract (MeChrSdEx), Chardonnay seed ethanol extract residue (40EtChrSdRes), Chardonnay seed methanol extract residue (MeChrSdRes), Chardonnay seed flour at 10%, 7%, and 3% by diet weight (10% ChrSd, 7% ChrSd, and 3% ChrSd, respectively), 10% White Riesling seed flour by diet weight (10% WRSd), and 10% Sauvignon Blanc seed flour by diet weight (10% SBSd) at the end of four weeks.

FIG. 16: Relative adipose gene expression of Example 3.

FIG. 17: Relative hepatic gene expression of Example 3.

Figure 18:
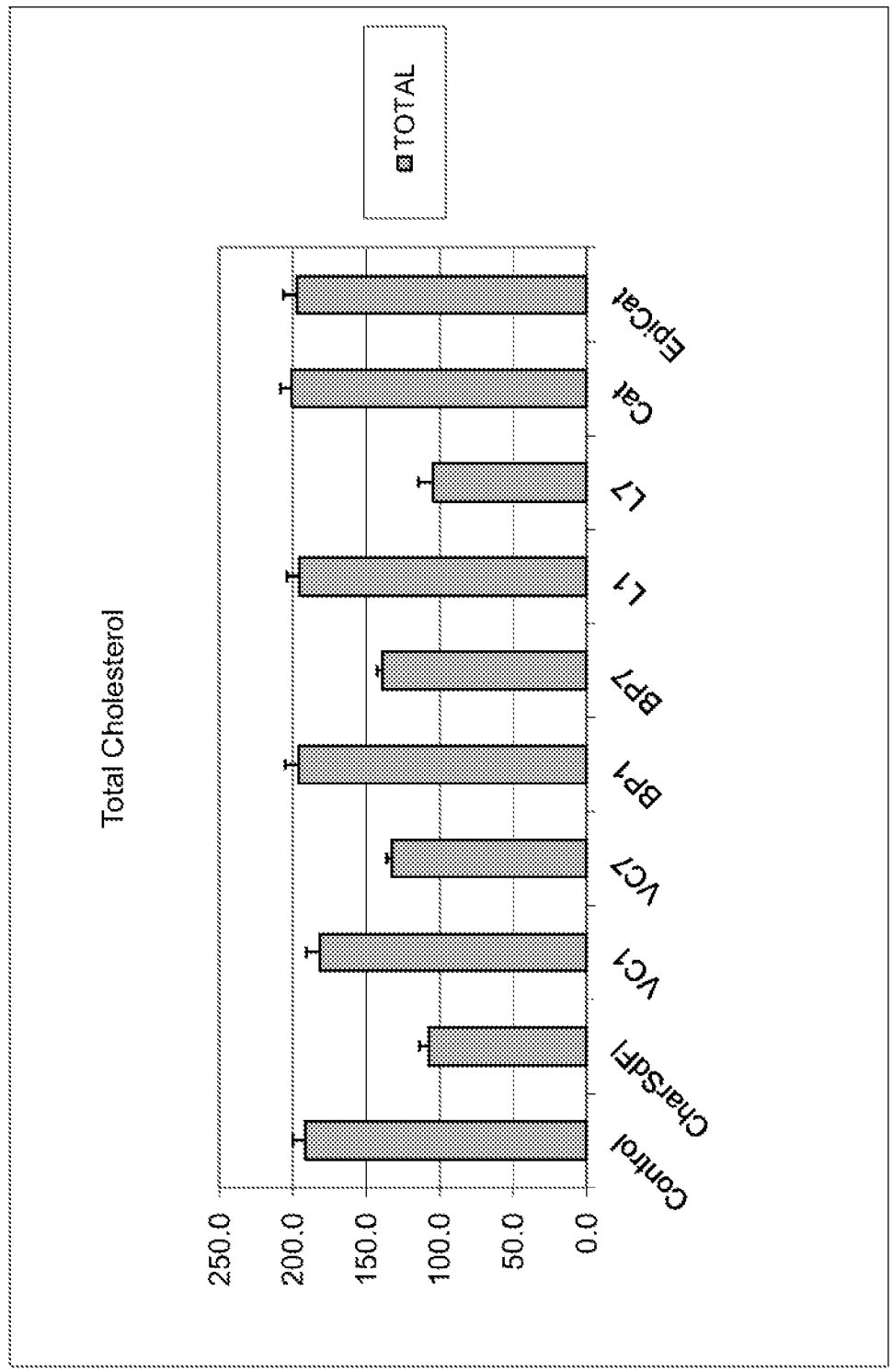

FIG. 18: Total plasma lipoprotein cholesterol levels of animals of Example 4 fed diets supplemented with Chardonnay seed flour (CharSdFl), Vitacost® grape seed extract (VC1 and VC7), Mega Natural® BP grape seed extract (BP1, BP7), Leucoselect® grape seed extract (L1, L7), catechin (Cat), and epicatechin (EpiCat) at the end of four weeks.

Figure 19:
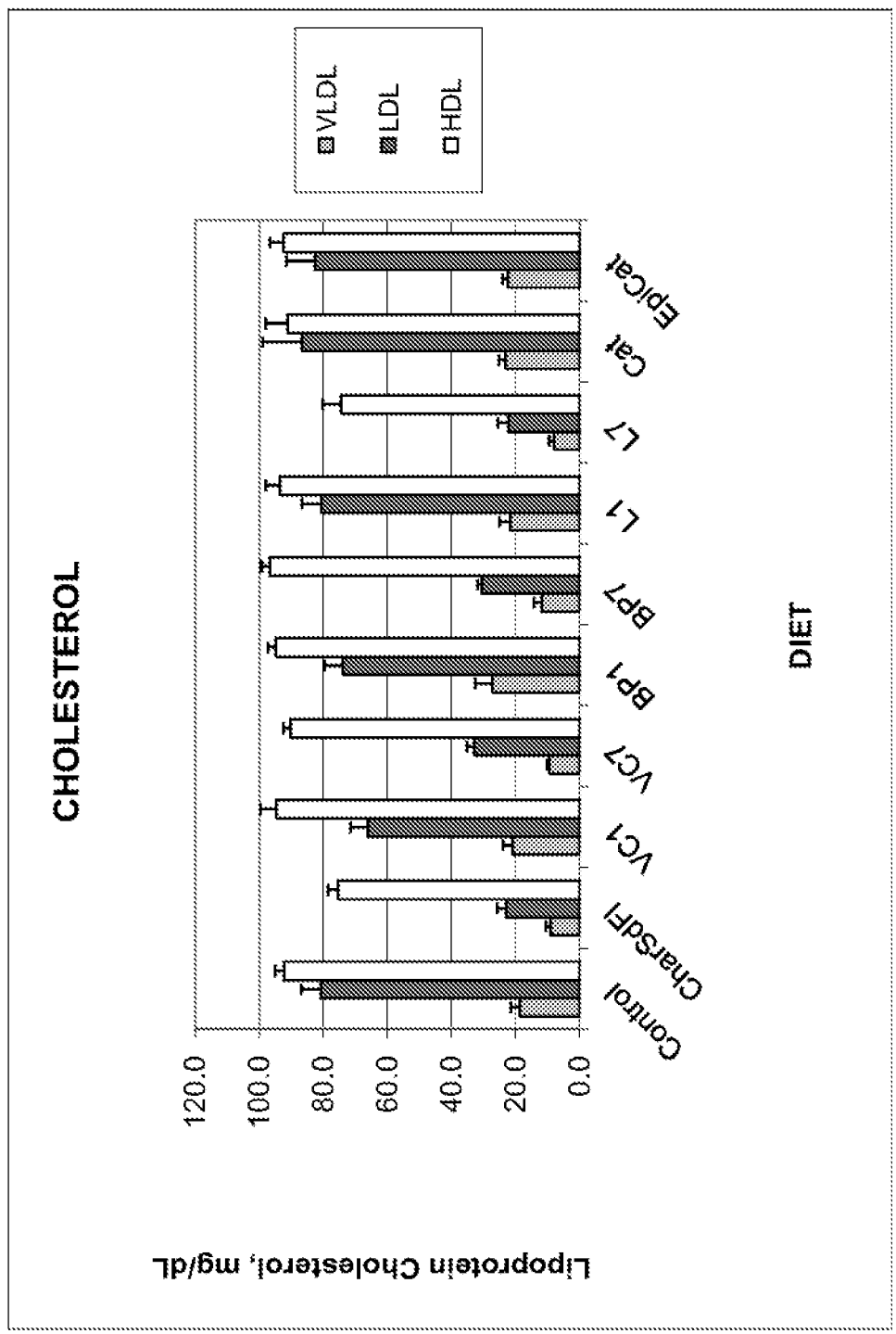

FIG. 19: VLDL, LDL, and HDL cholesterol levels of animals of Example 4 fed diets supplemented with Chardonnay seed flour (CharSdFl), Vitacost® grape seed extract (VC1 and VC7), Mega Natural® BP grape seed extract (BP1, BP7), Leucoselect® grape seed extract (L1, L7), catechin (Cat), and epicatechin (EpiCat) at the end of four weeks.

Figure 20:
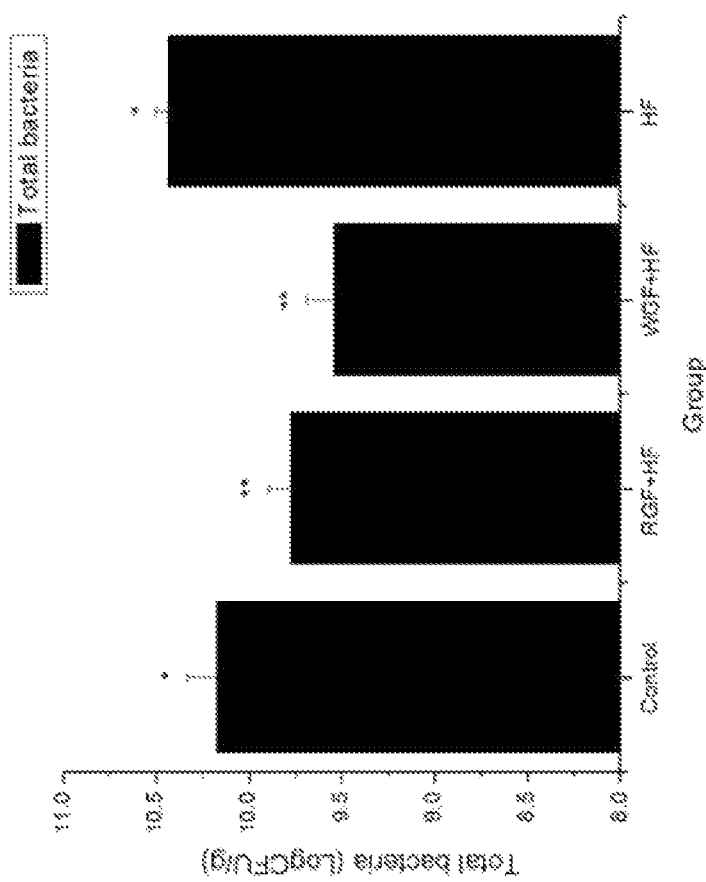

FIG. 20: Total fecal bacteria levels of animals of Example 5 fed a control diet, high fat diet supplemented with Cabernet seed flour (RGF+HF), high fat diet supplemented with Chardonnay seed flour (WGF+HF), and high fat control diet (HF).

Figure 21:
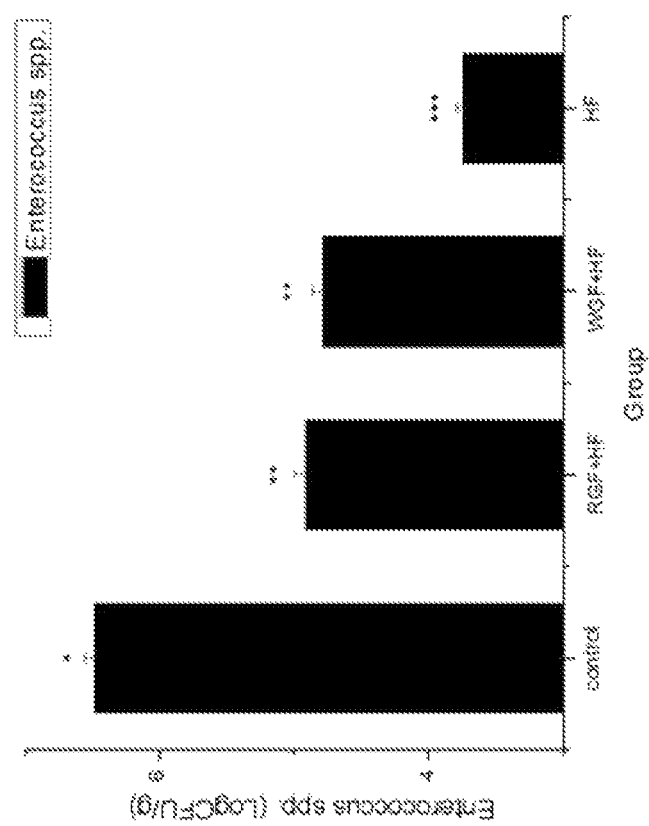

FIG. 21: *Enterococcus* spp. levels of animals of Example 5 fed a control diet, high fat diet supplemented with Cabernet seed flour (RGF+HF), high fat diet supplemented with Chardonnay seed flour (WGF+HF), and high fat control diet (HF).

Figure 22:
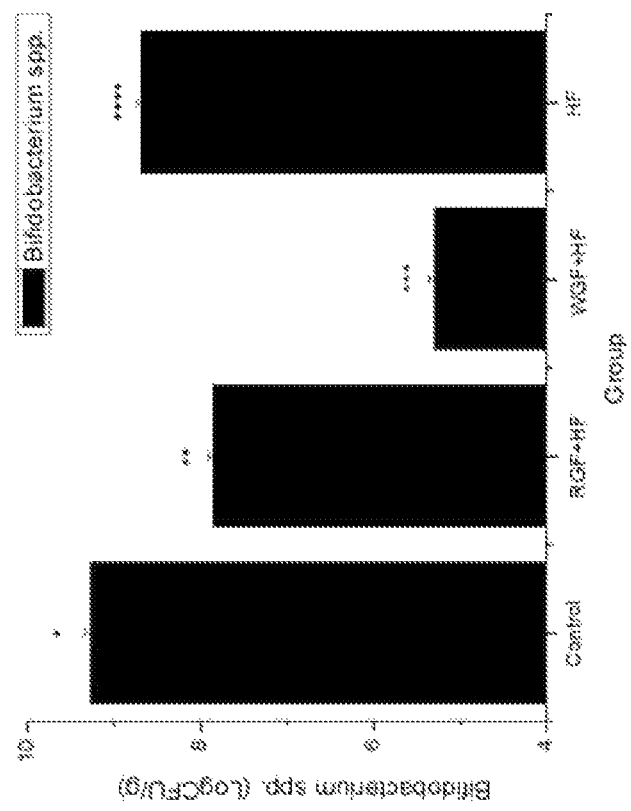

FIG. 22: *Bifidobacterium* spp. levels of animals of Example 5 fed a control diet, high fat diet supplemented with Cabernet seed flour (RGF+HF), high fat diet supplemented with Chardonnay seed flour (WGF+HF), and high fat control diet (HF).

Figure 23:
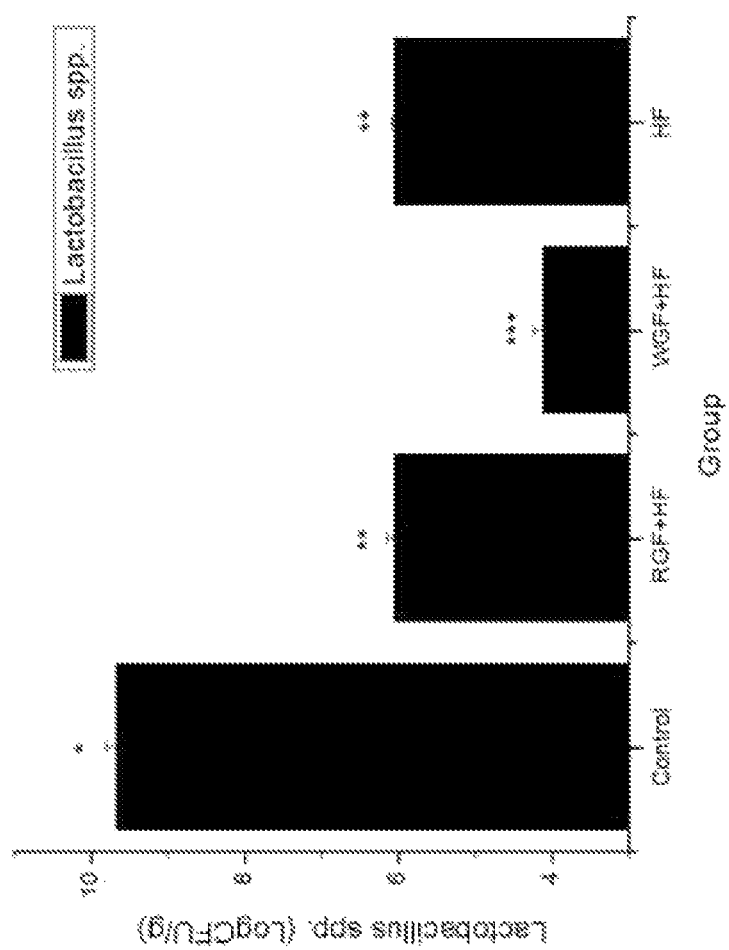

FIG. 23: *Lactobacillus* spp. levels of animals of Example 5 fed a control diet, high fat diet supplemented with Cabernet seed flour (RGF+HF), high fat diet supplemented with Chardonnay seed flour (WGF+HF), and high fat control diet (HF).

Figure 24:
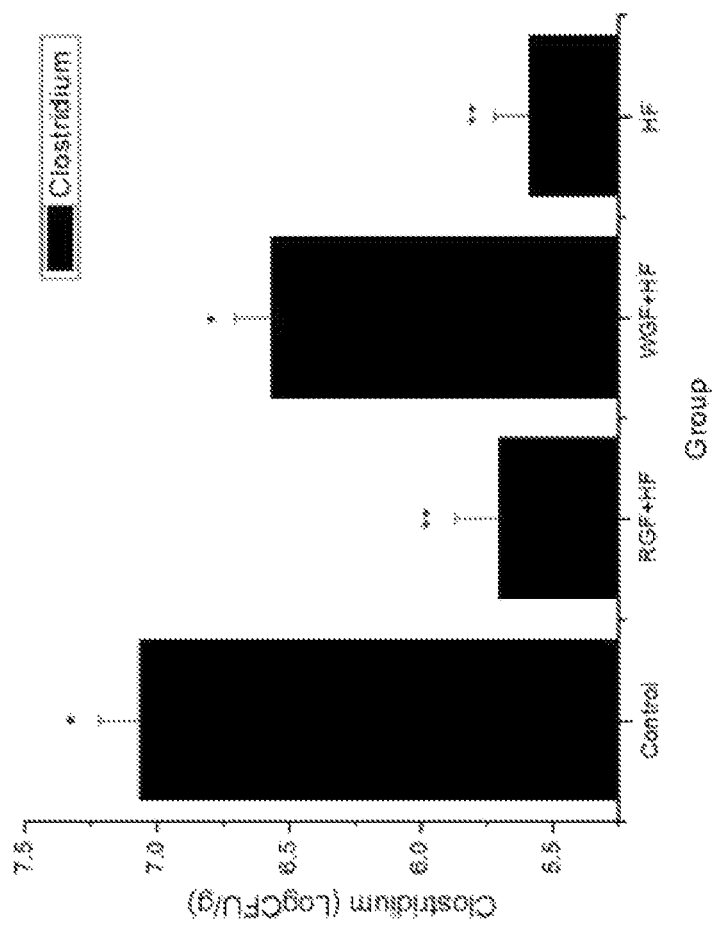

FIG. 24: *Clostridium* Cluster IV bacteria levels of animals of Example 5 fed a control diet, high fat diet supplemented with Cabernet seed flour (RGF+HF), high fat diet supplemented with Chardonnay seed flour (WGF+HF), and high fat control diet (HF).

Figure 25:
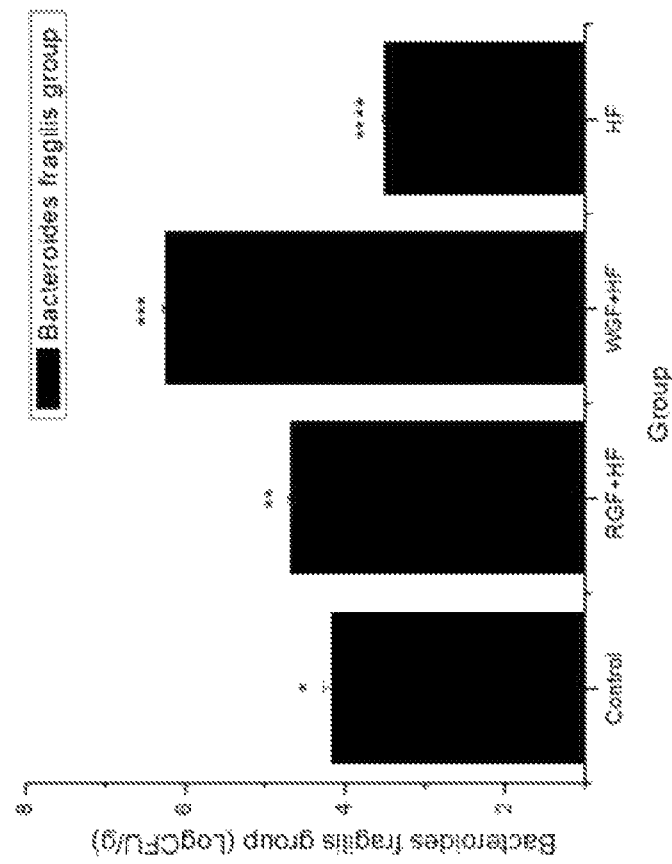

FIG. 25: *Bacteroides fragilis* group bacteria levels of animals of Example 5 fed a control diet, high fat diet supplemented with Cabernet seed flour (RGF+HF), high fat diet supplemented with Chardonnay seed flour (WGF+HF), and high fat control diet (HF).

Figure 26:
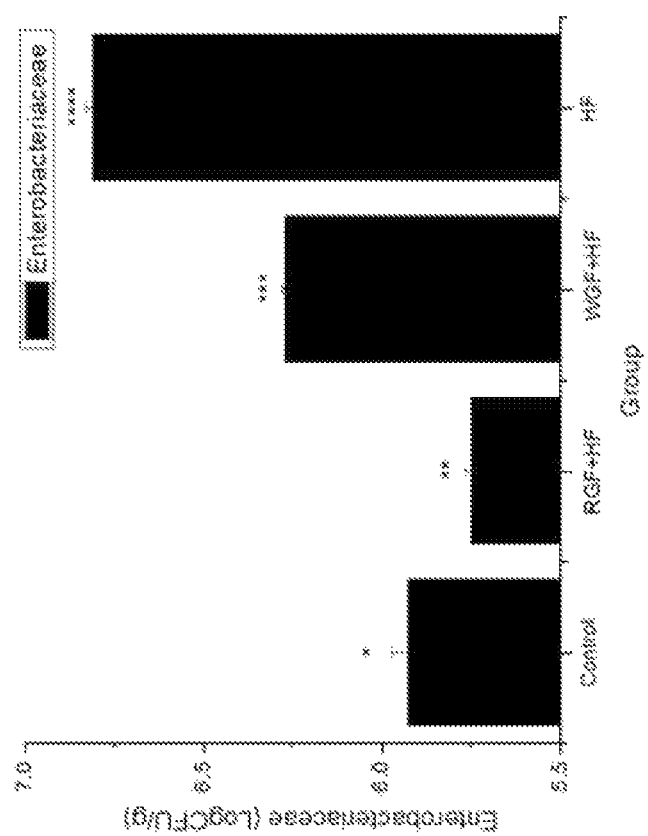

FIG. 26: Enterobacteriaceae levels of animals of Example 5 fed a control diet, high fat diet supplemented with Cabernet seed flour (RGF+HF), high fat diet supplemented with Chardonnay seed flour (WGF+HF), and high fat control diet (HF).

4. DETAILED DESCRIPTION

4.1. Chardonnay Seed Products

The present invention relates to Chardonnay seed products and methods of treating or preventing obesity and other conditions using Chardonnay seed products. Preferably, the Chardonnay seed products are produced from grapes grown in Winkler region climate types I-IV (Jones et al., 2010, Am. J. Enol. Vitic. 61(3):313-326). In some embodiments, the Chardonnay seed products are produced from grapes grown in the coastal valleys of Northern California, e.g., the Napa Valley and/or the Sonoma Valley. In another embodiment, the Chardonnay seed products are produced from grapes grown in other, hotter, inland valley vineyards, e.g., in Winkler region climate types IV-V. In a preferred embodiment, the Chardonnay seed product is from grapes grown in a coastal region.

In an embodiment, the Chardonnay seed products contain the defatted portion of Chardonnay seed, such as Chardonnay pomace meal, Chardonnay pomace flour, Chardonnay seed meal, or, most preferably, Chardonnay seed flour. In some embodiments, the Chardonnay seed product includes the contents of defatted Chardonnay seeds that are not extractable by an organic solvent, e.g., are not extractable by ethanol and/or methanol. In certain aspects, the Chardonnay seed product is prepared from seeds having an epicatechin content of at least 600 mg of epicatechin per 100 g of seeds or an epicatechin content of at least 700 mg of epicatechin per 100 g of seeds. In specific embodiments, the epicatechin content ranges from 600-800 mg/100 g of seeds or from 650-800 mg/100 g of seeds.

As used herein, "Chardonnay seed meal" is ground whole seeds and "Chardonnay seed flour" is ground seed after the oil has been extracted. Chardonnay seed flour may be obtained using the "cold press", "hot press" and solvent extraction processes as are known in the art to extract the oil from seeds yielding defatted seed flour. The meal or flour can be dried to the desired moisture content using conventional drying techniques suitable for drying food products.

The dried meal or flour is further ground under ambient temperature conditions to form Chardonnay seed powder having free-flowing particles. In an embodiment, the free-flowing particles can range from a size not exceeding 841 microns (20 mesh) to a size not exceeding 37 microns (400 mesh). In certain embodiments, the size does not exceed 20 mesh, 40 mesh, 60 mesh, 80 mesh, 100 mesh, 200 mesh, 300 mesh, or 400 mesh.

In an exemplary method, Chardonnay seed flour is made by separating and drying Chardonnay grape seeds, for example from the pomace produced after Chardonnay grapes are pressed to produce grape juice (e.g., to make wine). The grape seeds can be "cold-pressed" to defat them (producing Chardonnay seed oil as a byproduct). Grape seed flours are milled from the press cake after the oil is expelled. In one embodiment, after juicing the grape the seed is separated from the skins, cleaned, mechanically defatted, finely milled and sifted to create an 100 mesh (150 micron) flowable powder.

Chardonnay seed flour can also be purchased from Apres Vin (Yakima, Wash.), Botanical Oil Innovations (Spooner, Wis.) or Fruitsmart, Inc. (Grandview, Wash.). The FruitSmart Chardonnay seed flour is an 85 mesh flowable powder but can be further milled and sifted to produce a flour with a smaller particle size.

In an embodiment, skins, stems and leaves (the remainder of pomace) are removed from the seeds prior to pressing. Removal of the skins, stems, and leaves allows for optimal oil pressing.

"Chardonnay seed extract" is made by solvent extraction of Chardonnay seeds with a suitable solvent, such as ethanol or methanol. For example, "40EtChrSdEx" is a Chardonnay seed extract made using a 40% ethanol solution as the extraction solvent. The extraction process, in addition to the extract containing the solvent soluble components, also produces a residue of non-soluble solids.

4.2. Effective Amount

In an embodiment of the methods of the invention, the amount of Chardonnay seed flour consumed as a percentage of daily diet is at least 3%, at least 5%, or at least 8% by mass. Preferably, 5-10%, more preferably 7%, and in some embodiments 10% of the daily diet by mass is Chardonnay seed flour.

In an embodiment of the methods of the invention, the amount of Chardonnay seed flour consumed as a percentage of daily diet is at least 3%, at least 5%, or at least 8% of total calories consumed. Preferably, 5-10%, more preferably 7%, and in some embodiments 10% of the daily calories are from Chardonnay seed flour.

In another embodiment, the amount of Chardonnay seed flour consumed daily is at least 10 g, at least 15 g, at least 20 g, at least 25 g, at least 30 g, at least 35 g, at least 40 g, or at least 45 g. Preferably, 50 g of Chardonnay seed flour is consumed daily.

In another embodiment, the amount of Chardonnay seed flour consumed daily is at least 1 tablespoon, at least 2 tablespoons, at least 3 tablespoons, at least 4 tablespoons, or at least 5 tablespoons.

In another embodiment, the amount of Chardonnay seed flour consumed daily on a Chardonnay seed flour weight:body weight basis is at least 0.2 g/kg, at least 0.5 g/kg, or at least 0.7 g/kg. Preferably at least 1 g of Chardonnay seed flour per kg of body weight is consumed per day.

In certain aspects, an amount of Chardonnay seed flour is administered that is effective to modulate expression of one or more genes involved in fat, cholesterol, and/or bile metabolism. In specific embodiments, the amount is effective to increase expression of ACOX1 in hepatic tissue, to increase expression of CYP51 in hepatic tissue, to increase expression of CYP7a1 in hepatic tissue, to decrease expression of SCD1 in hepatic tissue, and/or to decrease expression of ABCG5 in hepatic tissue, for example by at least 10%, at least 20%, at least 50%, or at least 100%.

Chardonnay seed flour can be substituted with Chardonnay pomace meal, pomace flour, skin flour, seed extract, or seed meal in the methods of the invention. The amount of Chardonnay pomace meal, pomace flour, skin flour, seed extract, or seed meal that will need to be consumed daily to attain the same benefit as a given amount of Chardonnay seed flour can readily be determined by those skilled in the art. For example, it is expected that a subject will need to consume about three times as much Chardonnay skin flour to achieve the same benefit as a given amount of Chardonnay seed flour.

In certain embodiments, the Chardonnay seed product, e.g., Chardonnay seed flour, is taken at least twice a week, at least 3 times a week, or every other day. Preferably, the Chardonnay seed product is incorporated into the daily diet.

The Chardonnay seed product, e.g., Chardonnay seed flour, can be taken for an amount of time sufficient to treat and/or prevent a condition amenable to treatment and/or prevention by Chardonnay seed product as described herein. The Chardonnay seed product a can be taken for at least one week, at least 2 weeks, at least 3 weeks, at least one month, at least 2 months, at least 3 months, at least 6 months, at least a year, or indefinitely.

In certain embodiments of the methods, a second grape seed or grape skin product which is not a Chardonnay seed product is administered to the mammal. In certain aspects, the combination of Chardonnay seed product and second grape seed or grape skin product provides a therapeutic effect or health benefit which is greater than the effect of administration of Chardonnay seed product alone.

In other embodiments, the amount of Chardonnay seed product and amount of the second grape seed or grape skin product are selected so that the effect achieved is at least the same as the effect achieved by a given amount of Chardonnay seed product administered alone.

4.3. Chardonnay Seed Compositions

The Chardonnay seed products can be included in a variety of food products, such as nutritional beverages (e.g., nutritional shakes), baked goods (e.g., cookies, brownies, cake, breads, biscuits, crackers), puddings, confections (i.e., candy), snack foods (e.g., pretzels), ice cream, frozen confections and novelties, or non-baked, extruded food products such as bars, including health or energy bars. The Chardonnay seed product can also be provided as a nutritional supplement, either in tablet form or as a powder for use as a nutritional food additive.

In one embodiment, the Chardonnay seed product can be blended with other dry food materials for use in the preparation of food products enriched with Chardonnay seed products. Dry food materials include, for example, dry starch-containing materials, dry protein-containing materials or combinations thereof. Suitable starch-containing materials may be derived from, for example, rice, corn, soybeans, sunflower, canola, wheat, oats, rye, potato, or any combination thereof. Suitable dry protein-containing materials may be derived from for example, meat, milk, fish or any combination thereof. For baking applications, the Chardonnay seed product is suitable used in an amount ranging from 3% to 15% of the dry food material (e.g., white or whole wheat flour). The dry food may optionally also include additional ingredients such as vitamins, mineral fortifiers, salts, colors, flavors, flavor enhancers or sweeteners.

Chardonnay seed products can be incorporated into beverages, processed meats, frozen desserts, confectionery products, dairy-type products, sauce compositions, and cereal grain products. Beverage products include, for example, smoothies, infant formula, fruit juice beverages, yogurt beverages, coffee beverages, beer, dry beverage mixes, tea fusion beverages, sports beverages, soy liquors, soda, slushes, and frozen beverage mixes. Meat products include, for example, ground chicken products, water-added ham products, bologna, hot dogs, franks, chicken patties, chicken nuggets, beef patties, fish patties, surimi, bacon, luncheon meat, sandwich fillings, deli meats, meat snacks, meatballs, jerky, fajitas, bacon bits, injected meats, and bratwurst. Confectionery products include, for example, chocolates, mousses, chocolate coatings, yogurt coatings, cocoa, frostings, candies, energy bars, and candy bars. Frozen dessert products include, for example, ice cream, malts, shakes, popsicles, sorbets, and frozen pudding products. Dairy-type products include, for example, yogurt, cheese, ice cream, whipped topping, coffee creamer, cream cheese, sour cream, cottage cheese, butter, mayonnaise, milk-based sauces, milk-based salad dressings, and cheese curds. Cereal grain products include, for example, breads, muffins, bagels, pastries, noodles, cookies, pancakes, waffles, biscuits, semolina, chips, tortillas, cakes, crackers, breakfast cereals (including both ready-to-eat and cooked cereals), pretzels, dry bakery mixes, melba toast, breadsticks, croutons, stuffing, energy bars, doughnuts, cakes, popcorn, taco shells, fry coatings, batters, breading, crusts, brownies, pies, puffed soy cakes, crepes, croissants, flour, and polenta. Sauce compositions include salad dressings, nut butter spreads (e.g., peanut butter spreads), marinades, sauces, salsas, jams, cheese sauces, mayonnaise, tartar sauce, soy humus, dips, fruit syrups, and maple syrups. Sauce composition may also include a suspending agent to aid in maintaining the uniformity of the composition. Examples of suitable suspending agents include polysaccharides, such as starch, cellulose (e.g., microcrystalline cellulose) and carrageenan, and polyuronides, such as pectin. Gelatin is another example of a suspending agent which may be used in the beverage compositions as well. Examples of additional supplemented food products prepared using the premixes in accordance with the invention include tofu, formulated soy essence, powdered protein supplements, juice mixable protein supplements, foaming agents, clouding agents, baby foods, meatless balls, meat analogues, egg products (e.g., scrambled eggs), soups, chowders, broth, milk alternatives, soy-milk products, chili, spice mixes, sprinkles, soy whiz, salad topping, edible films, edible sticks, chewing gum, bacon bits, veggie bits, pizza crust barriers, soy pie, no-gas synthetic beans, soy helper, soy cotton candy, fruit bits, pizza rolls, mashed potatoes, spun soy protein fiber, soy roll-ups, extruded snacks, condiments, lotions, fries, gelatin dessert products, vitamin supplements, nutritional bars, dry cake, bread or muffin mixes, and microwavable instant dry mixes.

In a particular aspect, the Chardonnay seed product may be provided as an energy bar (suitable for consumption during physical activity) or a meal replacement bar. The energy bar or meal replacement bar can also contain one or more vitamin, mineral, food supplement, botanical, or plant or herb extracts or ingredients known in the art or used in energy bars or meal replacement bars, such as a fruit juice or extract, an herb or herb flavor, natural or artificial flavors, vitamins, minerals, anti-oxidant containing extracts, coenzyme Q, omega-3 fatty acids, guarana, caffeine, theobromine, maltodextrin, and protein. In some embodiments, the energy bar or meal replacement bar can have total available energy levels of carbohydrates/protein/fat of 40/30/30 respectively.

The energy and meal replacement bars can be further supplemented for athletic performance enhancement, mental energy or cognitive focus enhancement, and/or nutritional benefit. Exemplary supplements include, but are not limited to Vinpocetine, Vincamine *Ginkgo Biloba*, L-Arginine, Acetyl-L-Carnitine, Feverfew, DMAE (Dimethylaminoethanol), DMAE bitartrate, P-chlorophenoxyacetate, Vitamin B-Complex, *Ginseng*, 5 HTP (5-Hydroxytryptophan), L-Theanine, Androstenedione, L-Glutamine, L-Tyrosine, L-Glycine; L-lysine; Whey Protein; DHEA (Dehydroepiandrosterone).

In another aspect, the Chardonnay seed product may be provided in or added to a liquid or powder infant formula. The infant formula can contain a protein source, a fat source, and/or a carbohydrate source. The protein source can be, for example, dry or liquid cow's milk, whey and/or casein, or soy protein. The fat source can be, for example, dairy fat and/or one or more vegetable oils. The carbohydrate source can be, for example, lactose, glucose, or sucrose. The infant formula can additionally contain one or more vitamins, and/or one or more minerals. In an embodiment, the Chardonnay seed product may be added to a commercially available liquid or powder infant formula.

The Chardonnay seed composition can also contain an amount of a second grape seed or grape skin product which is not a Chardonnay seed product. In some embodiments, an amount of Chardonnay seed product is replaced in the Chardonnay seed composition with an amount of the second grape seed or grape skin product. The amount of second grape seed or grape skin product that will need to be added to the Chardonnay seed composition to attain the same benefit as a given amount of Chardonnay seed product can readily be determined by those skilled in the art.

4.4. Therapeutic Uses of Chardonnay Seed Flour Compositions

In accordance with the invention, a composition of the invention, comprising a Chardonnay seed flour composition, is administered to a subject, preferably a human subject, in which an increase in lipid metabolism is useful or desired. The subject can be in need of treatment or prevention of a cardiovascular disease, a dyslipidemia, a disorder of glucose metabolism, Alzheimer's Disease, Syndrome X, a PPAR-associated disorder, septicemia, a thrombotic disorder, obesity, pancreatitis, hypertension, a renal disease, cancer, inflammation, or impotence.

In another aspect of the invention, a composition of the invention, comprising a Chardonnay seed flour composition, is administered to a subject, preferably a human subject, in which modulation of the gut biome is useful or desired. In an embodiment, the subject can be in need of treatment or prevention of, for example, lactic acidosis, colitis, or colorectal cancer. In an embodiment, the subject is genetically susceptible to colon cancer.

In one embodiment, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the subject. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

In certain embodiments, the compositions of the invention are administered to a subject, preferably a human, as a preventative measure against such diseases. As used herein, "prevention" or "preventing" refers to a reduction of the risk of acquiring a given disease or disorder. In a preferred aspect, the compositions of the present invention are administered as a preventative measure to a subject, preferably a human having a genetic predisposition to a cardiovascular disease, a dyslipidemia, a dyslipoproteinemia, a disorder of glucose metabolism, Alzheimer's Disease, Syndrome X, a PPAR-associated disorder, septicemia, a thrombotic disorder, obesity, pancreatitis, hypertension, a renal disease, cancer, inflammation, or impotence. Examples of such genetic predispositions include but are not limited to the E4 allele of apolipoprotein E, which increases the likelihood of Alzheimer's Disease; a loss of function or null mutation in the lipoprotein lipase gene coding region or promoter (e.g., mutations in the coding regions resulting in the substitutions D9N and N291S; for a review of genetic mutations in the lipoprotein lipase gene that increase the risk of cardiovascular diseases, dyslipidemias and dyslipoproteinemias, see Hayden and Ma, 1992, Mol. Cell Biochem. 113:171-176); and familial combined hyperlipidemia and familial hypercholesterolemia.

In another preferred mode of the embodiment, the compositions of the invention are administered as a preventative measure to a subject having a non-genetic predisposition to a cardiovascular disease, a dyslipidemia, a dyslipoproteinemia, a disorder of glucose metabolism, Alzheimer's Disease, Syndrome X, a PPAR-associated disorder, septicemia, a thrombotic disorder, obesity, pancreatitis, hypertension, a renal disease, cancer, inflammation, or impotence. Examples of such non-genetic predispositions include but are not limited to cardiac bypass surgery and percutaneous transluminal coronary angioplasty, which often lead to restenosis, an accelerated form of atherosclerosis; diabetes in women, which often leads to polycystic ovarian disease; and cardiovascular disease, which often leads to impotence.

In certain embodiments, the mammal consumes a high-fat diet. In an embodiment, a high-fat diet is a diet in which at least 30%, 35%, or 40% of total daily calories are obtained from fat.

In certain embodiments, a second grape seed or grape skin product which is not Chardonnay seed flour is administered to the mammal to provide an effect which is greater than the effect of administration of Chardonnay seed flour alone.

4.4.1. Dyslipidemias

The present invention provides methods for the treatment or prevention of a dyslipidemia comprising administering to a subject a therapeutically effective amount of a Chardonnay seed flour composition.

As used herein, the term "dyslipidemias" refers to disorders that lead to or are manifested by aberrant levels of circulating lipids. To the extent that levels of lipids in the blood are too high, the compositions of the invention are administered to a subject to restore normal levels. Normal levels of lipids are reported in medical treatises known to those of skill in the art. For example, recommended blood levels of LDL, HDL, free triglycerides and others parameters relating to lipid metabolism can be found at the web sites of the American Heart Association and that of the National Cholesterol Education Program of the National Heart, Lung and Blood Institute. At the present time, the recommended level of HDL cholesterol in the blood is above 35 mg/dL; the recommended level of LDL cholesterol in the blood is below 130 mg/dL; the recommended LDL:HDL cholesterol ratio in the blood is below 5:1, ideally 3.5:1; and the recommended level of free triglycerides in the blood is less than 200 mg/dL.

Dyslipidemias which the Chardonnay seed flour compositions of the present invention are useful for preventing or treating include but are not limited to hyperlipidemia and low blood levels of high density lipoprotein (HDL) cholesterol. In certain embodiments, the hyperlipidemia for prevention or treatment by the compounds of the present invention is familial hypercholesterolemia; familial combined hyperlipidemia; reduced or deficient lipoprotein lipase levels or activity, including reductions or deficiencies resulting from lipoprotein lipase mutations; hypertriglyceridemia; hypercholesterolemia; high blood levels of ketone bodies (e.g. n-OH butyric acid); high blood levels of Lp(a) cholesterol; high blood levels of low density lipoprotein (LDL) cholesterol; high blood levels of very low density lipoprotein (VLDL) cholesterol and high blood levels of non-esterified fatty acids.

The present invention further provides methods for altering lipid metabolism in a subject, e.g., reducing LDL in the blood of a subject, reducing free triglycerides in the blood of a subject, increasing the ratio of HDL to LDL in the blood of a subject, and inhibiting saponified and/or non-saponified fatty acid synthesis, said methods comprising administering to the subject a Chardonnay seed flour composition in an amount effective alter lipid metabolism.

4.4.2. Cardiovascular Diseases

The present invention provides methods for the treatment or prevention of a cardiovascular disease, comprising administering to a subject a therapeutically effective amount of a Chardonnay seed flour composition. As used herein, the term "cardiovascular diseases" refers to diseases of the heart and circulatory system. These diseases are often associated with dyslipoproteinemias and/or dyslipidemias. Cardiovascular diseases which the compositions of the present invention are useful for preventing or treating include but are not limited to arteriosclerosis; atherosclerosis; stroke; ischemia; endothelium dysfunctions, in particular those dysfunctions affecting blood vessel elasticity; peripheral vascular disease; coronary heart disease; myocardial infarcation; cerebral infarction and restenosis.

4.4.3. Dyslipoproteinemias

The present invention provides methods for the treatment or prevention of a dyslipoproteinemia comprising administering to a subject a therapeutically effective amount of a Chardonnay seed flour composition.

As used herein, the term "dyslipoproteinemias" refers to disorders that lead to or are manifested by aberrant levels of circulating lipoproteins. To the extent that levels of lipoproteins in the blood are too high, the compositions of the invention are administered to a subject to restore normal levels. Conversely, to the extent that levels of lipoproteins in the blood are too low, the compositions of the invention are administered to a subject to restore normal levels. Normal levels of lipoproteins are reported in medical treatises known to those of skill in the art.

Dyslipoproteinemias which the compositions of the present invention are useful for preventing or treating include but are not limited to high blood levels of LDL; high blood levels of apolipoprotein B (apo B); high blood levels of Lp(a); high blood levels of apo(a); high blood levels of VLDL; low blood levels of HDL; reduced or deficient lipoprotein lipase levels or activity, including reductions or deficiencies resulting from lipoprotein lipase mutations; hypoalphalipoproteinemia; lipoprotein abnormalities associated with diabetes; lipoprotein abnormalities associated with obesity; lipoprotein abnormalities associated with Alzheimer's Disease; and familial combined hyperlipidemia.

The present invention further provides methods for reducing apo C-II levels in the blood of a subject; reducing apo C-III levels in the blood of a subject; elevating the levels of HDL associated proteins, including but not limited to apo A-I, apo A-II, apo A-IV and apo E in the blood of a subject; elevating the levels of apo E in the blood of a subject, and promoting clearance of triglycerides from the blood of a subject, said methods comprising administering to the subject a Chardonnay seed flour composition in an amount effective to bring about said reduction, elevation or promotion, respectively.

4.4.4. Glucose Metabolism Disorders

The present invention provides methods for the treatment or prevention of a glucose metabolism disorder, comprising administering to a subject a therapeutically effective amount of a Chardonnay seed flour composition. As used herein, the term "glucose metabolism disorders" refers to disorders that lead to or are manifested by aberrant glucose storage and/or utilization. To the extent that indicia of glucose metabolism (i.e., blood insulin, blood glucose) are too high, the compositions of the invention are administered to a subject to restore normal levels. Conversely, to the extent that indicia of glucose metabolism are too low, the compositions of the invention are administered to a subject to restore normal levels. Normal indicia of glucose metabolism are reported in medical treatises known to those of skill in the art.

Glucose metabolism disorders which the compositions of the present invention are useful for preventing or treating include but are not limited to impaired glucose tolerance; insulin resistance; insulin resistance related breast, colon or prostate cancer; diabetes, including but not limited to non-insulin dependent diabetes mellitus (NIDDM), insulin dependent diabetes mellitus (IDDM), gestational diabetes mellitus (GDM), and maturity onset diabetes of the young (MODY); pancreatitis; hypertension; polycystic ovarian disease; and high levels of blood insulin and/or glucose.

The present invention further provides methods for altering glucose metabolism in a subject, for example to increase insulin sensitivity and/or oxygen consumption of a subject, said methods comprising administering to the subject a Chardonnay seed flour composition in an amount effective to alter glucose metabolism.

4.4.5. Modulation of Gut Bacteria

Human gut biomes have been classified into three enterotypes according to the species dominating the bacterial population. These enterotypes are *Bacteroides*, Ruminococcus, and *Prevotella*. The *Bacteroides* enterotype has been found to make several vitamins, including C and H, while the *Prevotella* enterotype has been found to make folic acid and vitamin B 1.

The present invention provides methods for modulating gut bacteria levels, comprising administering to a subject an amount of a Chardonnay seed flour composition effective to modulate gut bacteria levels. As used herein, "modulate gut bacteria levels" refers to (i) a decrease in the amount of total gut bacteria levels, and/or (ii) an increase or a decrease in bacteria levels of a subset of the total gut bacteria. A subset of the total gut bacteria can be a single species, a genus, a family, an order, a class, a phylum, or a combination of more than one of the foregoing.

It may be desirable, for example, to modulate the levels of gut bacteria levels in infants born by cesarean section because bacterial colonization of the gut is delayed in infants born by cesarean section as compared to infants born by vaginal delivery. Differences in gut microbiota can persist for up to six months after birth (Grolund, M. et al., *Journal of Pediatric Gastroenterology & Nutrition*, (1999), vol. 28(1):19-25). For example, infants born by cesarean delivery are significantly less colonized with bacteria of the *Bacteroides fragilis* group than infants born by vaginal delivery at 6 months of age. Seven days after birth, infants born by cesarean delivery have higher levels of Enterobacteriaceae bacteria *Citrobacter* spp. and *E. coli* as a percentage of total gut bacteria compared to infants born by vaginal delivery (Pandey, P. et al., *J. Biosci*. (2012) vol. 37(6):989-998). Chardonnay seed flour compositions can be used to increase the level of *Bacteroides fragilis* group bacteria and *Clostridium* spp., and decrease the level of Enterobacteriaceae bacteria in infants born by cesarean delivery, for example, in order to promote the formation of a gut biome that more closely resembles the gut microbiome of infants born vaginally.

Chardonnay seed flour compositions can also be used to treat or prevent lactic acidosis by reducing the amount of lactic acid producing bacteria, e.g., *Lactobacillus* spp., in the gut. Chardonnay seed flour compositions can also be used to promote colonic health by increasing the level of *Clostridium* spp. in the gut. *Clostridium* bacteria produce butyrate, which is the preferred energy source in the colonic mucosa. Butyrate protects against colitis and colorectal cancer, and is important for the normal development of colonic epithelial cells. Shen, J. et al., *Applied and Environmental Microbiology*, vol. 72:5232-5238 (2006).

Chardonnay seed flour compositions can also be used to decrease levels of *Bifidobacterium* spp. in the gut. However, if lowering the level of *Bifidobacterium* spp. is not desired but another therapeutic benefit of Chardonnay seed flour administration is desired, a probiotic supplement containing one or more *Bifidobacterium* species may be administered to the subject to raise the levels of *Bifidobacterium* species in the gut of the subject. Examples of *Bifidobacterium* species that may be administered in a probiotic supplement include *Bifidobacterium bifidum, Bifidobacterium breve*, and *Bifidobacterium longum*. The probiotic supplement can include additional bacterial species, for example, one or more of *Lactobacillus acidophilus, Lactobacillus plantarum, Lactobacillus salivarious, Lactobacillus casei, Lactobacilus paracasei, Lactobacillus rhamnosus*, and *Streptococcus thermophilus*.

In an embodiment, the subject is identified as having an enterotype which is *Bacteroides*, Ruminococcus, or *Prevotella*. In an embodiment, the subject has a *Bacteroides* enterotype. In an embodiment, the subject has a Ruminococcus enterotype. In an embodiment, the subject has a *Prevotella* enterotype.

4.5. Therapeutic Uses of Chardonnay Seed Extract Compositions

In accordance with the invention, a composition of the invention, comprising a Chardonnay seed extract composition, is administered to a subject, preferably a human subject, for each of the therapeutic uses described in Section 4.4. Chardonnay seed extract has similar biological effects as Chardonnay seed flour (data not shown). In order to achieve a benefit which in comparable to the benefit obtained by using an amount of Chardonnay seed flour, the amount of Chardonnay seed extract administered should be an amount which provides 2-5 times the catechin levels of the amount of Chardonnay seed flour. Specific amounts of Chardonnay seed extract that will need to be consumed daily to attain the same benefit as a given amount of Chardonnay seed flour can readily be determined by those skilled in the art.

5. EXAMPLE 1: COMPARISON OF HEALTH BENEFITS OF CHARDONNAY, SAUVIGNON BLANC AND WHITE RIESLING PRODUCTS 5.1. Materials & Methods 5.1.1. Hamsters and Diets Male Golden Syrian hamsters (~80 g, LVG strain, Charles River) were acclimatized and given water and a 5001 rodent diet (LabDiet, PMI International; protein, 239 g/kg; fat, 50 g/kg; non-nitrogenous substances, 487 g/kg; crude fiber, 51 g/kg; ash, 70 g/kg; energy, 17 MJ/kg; and sufficient amounts of minerals and vitamins for healthy maintenance) ad libitum for 1 week prior to the initiation of the experimental diets. Hamsters were weighed and randomized into 2 groups of 15 hamsters each and were fed high-fat diets ad libitum containing either 10% (by weight) Chardonnay, Cabernet or Syrah grape seed flour or grape skin flour or the control (Diets) for 4 weeks. Grapes from which the flours were produced were grown in the coastal valleys of Northern California. The compositions of the flours are shown in FIG. 1. Diets consisted of 18% of energy as protein, 43% as carbohydrate, and 39% as fat supplemented with 0.1% cholesterol (FIG. 2) GenOil refers to a commercially available grape seed oil from an unspecified grape variety. Body weights were recorded weekly and food intake was monitored twice per week. The study was approved by the Animal Care and Use Committee, Western Regional Research Center, USDA, Albany, Calif.

5.1.2. Plasma and Tissue Collection

Hamsters were fasted for 12 hours and anesthetized with Isoflurane (Phoenix Pharmaceutical). Blood was collected by cardiac puncture with syringes previously rinsed with potassium EDTA solution (15% wt:v) and plasma was separated after centrifugation at 2000×g for 30 minutes at 4° C. Livers were collected, weighed, and immediately frozen in liquid nitrogen for analysis.

5.1.3. Plasma Biomarker Analysis

Cholesterol in plasma lipoproteins were determined by size-exclusion chromatography as previously described (German et al., 1996. Nutr Res. 1996; 16:1239-49). Plasma triglycerides, total cholesterol, free cholesterol, and glucose were determined by enzymatic colorimetric assays using a Roche Diagnostics/Hitachi 914 Clinical Analyzer with assay kits (Roche Diagnostics and Wako Chemicals). Plasma concentrations of adiponectin (B-bridge International) and insulin (Mercodia) of feed-deprived hamsters were determined using mouse adiponectin and ultra-sensitive rat insulin immunoassay kits as previously described (Hung et al., 2009, J. Diabetes 1:194-206). Blood glucose concentrations in feed-deprived hamsters were measured in tail vein samples using a OneTouch Ultrameter (LifeScan).

5.1.4. Hepatic Lipid Analysis

Lyophilized, ground liver samples were extracted using an accelerated solvent extractor (Dionex) at 100° C.; 13.8 MPa with 75/25 hexane/2-propanol. The sample extract was analyzed on a Roche Diagnostic/Hitachi 914 clinical analyzer (Roche Diagnostics) to determine hepatic triglycerides, total cholesterol, and free cholesterol using the kits described above.

5.1.5. Fecal Bile Acids and Sterol Analysis

Feces were collected for 3 consecutive days immediately prior to when the hamsters were killed and were lyophilized, milled, and stored at −20° C. Bile acids and sterols were determined by HPLC as described previously (Hong et al., 2007, J Agric Food Chem. 55:9750-7).

5.1.6. Statistical Analysis

All data are expressed as means±SE. Differences between control and different diet groups were determined by 2-tailed Student's t tests. When variances of each group were unequal, significance of differences was determined using the Welch's test. Pearson correlation coefficients were calculated for investigating relationships of plasma total cholesterol, plasma adiponectin concentrations, hepatic cholesterol, and triglyceride concentrations with the expression of hepatic genes (JMP 7 statistical program, SAS Institute). Significance was defined at $P<0.05$.

5.2. Results

The animals fed Chardonnay seed flour had significantly decreased weight compared to animals fed the other diets (FIGS. 3-4). Animals fed the Chardonnay seed flour diet had an average weight of about 97 grams after four weeks. Animals fed the control diet had an average weight of about 110 grams after four weeks.

Although the Chardonnay seed flour treatment animals weighed less than control animals, the Chardonnay seed flour treatment animals ate more (FIG. 5), both in terms of volume (FIG. 6) and calories (FIG. 7).

Animals fed the Chardonnary seed flour diet showed the greatest decrease in VLDL (66%) and LDL (50%) cholesterol (FIG. 8). Blood glucose showed a slight reduction (FIG. 9).

Chardonnay seed flour lowered liver weights and epididimal adipose tissue (EA) weight 30% and 20%, respectively (FIG. 10).

These data show that Chardonnay seed flour was the obvious standout among grape products tested. Chardonnay skin flour showed a similar trend but not as great a benefit as Chardonnay seed flour.

6. EXAMPLE 2: COMPARISON OF HEALTH BENEFITS OF CHARDONNAY, SAUVIGNON BLANC AND WHITE RIESLING PRODUCTS 6.1. Materials & Methods 6.1.1. Hamsters and Diets Male Golden Syrian hamsters (~80 g, LVG strain, Charles River) were acclimatized and given water and a 5001 rodent diet (LabDiet, PMI International; protein, 239 g/kg; fat, 50 g/kg; non-nitrogenous substances, 487 g/kg; crude fiber, 51 g/kg; ash, 70 g/kg; energy, 17 MJ/kg; and sufficient amounts of minerals and vitamins for healthy maintenance) ad libitum for 1 week prior to the initiation of the experimental diets. Hamsters were weighed and randomized into 10 groups of 10 hamsters each and were fed high-fat diets ad libitum containing Chardonnay seed ethanol extract, Chardonnay seed methanol extract, Chardonnay seed ethanol extracted residue, Chardonnay seed methanol extracted residue, 10% (by weight) Chardonnay seed flour, 10% (by weight) Sauvignon Blanc seed flour, 10% (by weight) White Riesling seed flour, 7% (by weight) Chardonnay seed flour, 3% (by weight) Chardonnay seed flour, or a control diet for 4 weeks. Grapes from which the flours were produced were grown in the coastal valleys of Northern California. Ethanol extracts and extracted residues were prepared by a "tea extraction method" comprising the following steps: (1) solvent (1625 ml of 40% ethanol in distilled water) was added to 325 g Chardonnay seed flour and shaken at 80° C. for two hours; (2) the mixture from step (1) was then filtered through Whatman 1 filter paper; (3) ethanol was then removed from the filtrate from step (2) on a rotovac; (4) the solution from step (3) and filter cake from step (2) were frozen and freeze dried to produce Chardonnay seed ethanol extract and Chardonnay seed ethanol extracted residue, respectively. Similar procedures were used to produce Chardonnay seed methanol extract and Chardonnay seed methanol extracted residue.

Diets consisted of 18% of energy as protein, 43% as carbohydrate, and 39% as fat supplemented with 0.1% cholesterol. Body weights were recorded weekly and food intake was monitored twice per week. The study was approved by the Animal Care and Use Committee, Western Regional Research Center, USDA, Albany, Calif.

6.1.2. Plasma and Tissue Collection

Hamsters were fasted for 12 hours and anesthetized with Isoflurane (Phoenix Pharmaceutical). Blood was collected by cardiac puncture with syringes previously rinsed with potassium EDTA solution (15% wt:v) and plasma was separated after centrifugation at 2000×g for 30 min at 4° C. Livers were collected, weighed, and immediately frozen in liquid nitrogen for analysis.

6.1.3. Plasma Biomarker Analysis

Cholesterol in plasma lipoproteins were determined by size-exclusion chromatography as previously described (German et al., 1996, Nutr Res. 16:1239-49). Plasma triglycerides, total cholesterol, free cholesterol, and glucose were determined by enzymatic colorimetric assays using a Roche Diagnostics/Hitachi 914 Clinical Analyzer with assay kits (Roche Diagnostics and Wako Chemicals). Plasma concentrations of adiponectin (B-bridge International) and insulin (Mercodia) of feed-deprived hamsters were determined using mouse adiponectin and ultra-sensitive rat insulin immunoassay kits as previously described (Hung et al., 2009, J Diabetes. 1:194-206). Blood glucose concentrations in feed-deprived hamsters were measured in tail vein samples using a OneTouch Ultrameter (LifeScan).

6.1.4. Hepatic Lipid Analysis

Lyophilized, ground liver samples were extracted using an accelerated solvent extractor (Dionex) at 100° C.; 13.8 MPa with 75/25 hexane/2-propanol. The sample extract was analyzed on a Roche Diagnostic/Hitachi 914 clinical analyzer (Roche Diagnostics) to determine hepatic triglycerides, total cholesterol, and free cholesterol using the kits described above.

6.1.5. Fecal Bile Acids and Sterol Analysis

Feces were collected for 3 consecutive days immediately prior to when the hamsters were killed and were lyophilized, milled, and stored at −20° C. Bile acids and sterols were determined by HPLC as described previously (Hong et al., 2007, Agric Food Chem. 55:9750-7).

6.1.6. Statistical Analysis

All data are expressed as means±SE. Differences between control and different diet groups were determined by 2-tailedStudent's t tests. When variances of each group were unequal, significance of differences was determined using the Welch's test. Pearson correlation coefficients were calculated for investigating relationships of plasma total cholesterol, plasma adiponectin concentrations, hepatic cholesterol, and triglyceride concentrations with the expression of hepatic genes (JMP 7 statistical program, SAS Institute). Significance was defined at $P<0.05$.

6.2. Results

Chardonnay seed flour at 10% by weight of the diet showed reproducible results with Example 1. Animals fed the diet with Chardonnay seed flour at 10% by weight of the diet had the least weight gain on a 35% fat diet compared to the control animals.

Chardonnay seed flour showed a dose-response. Animals were fed 10%, 7% or 3% Chardonnay seed flour as part of their diet for 4 weeks. Increasing response, indicated as weight difference, was observed; the more the animals ate the less weight they added (FIG. 12).

Chardonnay seed extract showed some effect on weight but not as dramatic as the direct addition of Chardonnay seed flour.

Chardonnay seed extracts and Chardonnay seed extract residues showed some effect on cholesterol levels (FIG. 13) and LDL/HDL ratio (FIG. 14), but not as dramatic as the direct addition of Chardonnay seed flour. Similarly, the Chardonnay seed extracts showed some effect on organ weight (FIG. 15), but not as dramatic as the direct addition of Chardonnay seed flour.

Other white seed flours; e.g. Sauvignon Blanc or White Riesling showed little to no difference in weights compared to the control diets. Chardonnay has been compared side by side with four other varietals and is a clear standout.

7. EXAMPLE 3: EFFECTS OF CHARDONNAY SEED FLOUR ON RELATIVE ADIPOSE AND HEPATIC GENE EXPRESSION

7.1. Materials & Methods

7.1.1. Hamsters and Diets

Male Golden Syrian hamsters (~80 g, LVG strain, Charles River) were acclimatized and given water and a 5001 rodent diet (LabDiet, PMI International; protein, 239 g/kg; fat, 50 g/kg; non-nitrogenous substances, 487 g/kg; crude fiber, 51 g/kg; ash, 70 g/kg; energy, 17 MJ/kg; and sufficient amounts of minerals and vitamins for healthy maintenance) ad libitum for 1 week prior to the initiation of the experimental diets. Hamsters were weighed and randomized into 2 groups and fed high-fat diets ad libitum containing either 10% (by weight) Chardonnay grape seed flour or a control diet for 4 weeks. Grapes from which the flours were produced were grown in the coastal valleys of Northern California. Diets consisted of 18% of energy as protein, 43% as carbohydrate, and 39% as fat supplemented with 0.1% cholesterol. Body weights were recorded weekly and food intake was monitored twice per week. The study was approved by the Animal Care and Use Committee, Western Regional Research Center, USDA, Albany, Calif.

7.1.2. mRNA Analysis

Quantitative PCR (qPCR) was used to measure mRNA expression of selected genes of the inflammation, cholesterol, bile acid, and fatty acid pathways in adipose and liver samples from hamsters fed either the Chardonnay seed flour supplemented diet or the control diet.

7.1.3. Statistical Analysis

All data are expressed as averages±SD. Averages shown are relative values comparing mRNA levels in adipose or liver tissue from hamsters fed a diet supplemented with Chardonnay seed flour to mRNA levels in adipose or liver tissue from hamsters fed the control diet.

7.2. Results

Relative gene expression levels comparing gene expression in adipose tissue from hamsters fed a diet supplemented with Chardonnay seed flour to gene expression in adipose tissue from hamsters fed the control diet are shown in FIG. 16. Relative gene expression levels comparing gene expression in hepatic tissue from hamsters fed a diet supplemented with Chardonnay seed flour to gene expression in hepatic tissue from hamsters fed the control diet are shown in FIG. 17.

Hepatic ACOX1, CYP51, and CYP7a1 gene expression was notably elevated in hamsters fed the Chardonnay seed flour supplemented diet, while hepatic ABCG5 and SCD1 gene expression was notably decreased in hamsters fed the Chardonnay seed flour supplemented diet.

ACOX1 is involved in the regulation of fat oxidation, CYP51 is involved in the regulation of cholesterol biosynthesis, CYP7a1 is involved in the regulation of bile acid synthesis, SCD1 is involved in fat synthesis, and ABCG5 is involved in the transport of cholesterol back into the intestine. Accordingly, the results suggest that a diet supplemented with Chardonnay seed flour may reduce cholesterol and/or bile re-absorption, leading to reduced levels in the liver. The results further suggest that a diet supplemented with Chardonnay seed flour may reduce weight gain by hepatic gene up-regulation for fat oxidation (ACOX1) and/or by down-regulation of fat synthesis (SCD1).

8. EXAMPLE 4: COMPARISON OF HEALTH BENEFITS OF CHARDONNAY SEED FLOUR AND CHARDONNAY GRAPE SEED EXTRACT TO COMMERCIALLY AVAILABLE GRAPE SEED EXTRACTS 8.1. Materials & Methods 8.1.1. Hamsters and Diets Male Golden Syrian hamsters (~80 g, LVG strain, Charles River) were acclimatized and given water and a 5001 rodent diet (LabDiet, PMI International; protein, 239 g/kg; fat, 50 g/kg; non-nitrogenous substances, 487 g/kg; crude fiber, 51 g/kg; ash, 70 g/kg; energy, 17 MJ/kg; and sufficient amounts of minerals and vitamins for healthy maintenance) ad libitum for 1 week prior to the initiation of the experimental diets. All grape seed extracts were characterized by HPLC methods and their feeding amounts were adjusted to provide the same amount of catechin as a 7% (w/w) Chardonnay seed flour. Hamsters were weighed and randomized into 10 groups of 8 hamsters each and were fed high-fat diets ad libitum containing 7% (by weight) Chardonnay seed flour (1 group), Vitacost® grape seed extract (2 groups), Mega Natural® BP grape seed extract (2 groups), Leucoselect® grape seed extract (2 groups), catechin (approximately 0.000785 g/g diet) (1 group), epicatechin (approximately 0.00104 g/g diet) (1 group), or a control diet (1 group) for 4 weeks. Catechin levels were used to normalize each grape seed extract to the amount of Chardonnay seed flour. Epicatechin and catechin were included in the chow diet as controls for these compounds, which were implicated in other studies to be responsible for blood pressure and lipid regulation. Grapes from which the Chardonnay seed flour was produced were grown in the coastal valleys of Northern California. Diets consisted of 18% of energy as protein, 43% as carbohydrate, and 39% as fat supplemented with 0.1% cholesterol. Body weights were recorded weekly and food intake was monitored twice per week. The study was approved by the Animal Care and Use Committee, Western Regional Research Center, USDA, Albany, Calif.

8.1.2. Plasma and Tissue Collection

Hamsters were fasted for 12 hours and anesthetized with Isoflurane (Phoenix Pharmaceutical). Blood was collected by cardiac puncture with syringes previously rinsed with potassium EDTA solution (15% wt:v) and plasma was separated after centrifugation at 2000×g for 30 minutes at 4° C. Livers were collected, weighed, and immediately frozen in liquid nitrogen for analysis.

8.1.3. Plasma Biomarker Analysis

Cholesterol in plasma lipoproteins were determined by size-exclusion chromatography as previously described (German et al., 1996. Nutr Res. 1996; 16:1239-49). Plasma triglycerides, total cholesterol, free cholesterol, and glucose were determined by enzymatic colorimetric assays using a Roche Diagnostics/Hitachi 914 Clinical Analyzer with assay kits (Roche Diagnostics and Wako Chemicals). Plasma concentrations of adiponectin (B-bridge International) and insulin (Mercodia) of feed-deprived hamsters were determined using mouse adiponectin and ultra-sensitive rat insulin immunoassay kits as previously described (Hung et al., 2009, J. Diabetes 1:194-206). Blood glucose concentrations in feed-deprived hamsters were measured in tail vein samples using a OneTouch Ultrameter (LifeScan).

8.1.4. Hepatic Lipid Analysis

Lyophilized, ground liver samples were extracted using an accelerated solvent extractor (Dionex) at 100° C.; 13.8 MPa with 75/25 hexane/2-propanol. The sample extract was analyzed on a Roche Diagnostic/Hitachi 914 clinical analyzer (Roche Diagnostics) to determine hepatic triglycerides, total cholesterol, and free cholesterol using the kits described above.

8.1.5. Fecal Bile Acids and Sterol Analysis

Feces were collected for 3 consecutive days immediately prior to when the hamsters were killed and were lyophilized, milled, and stored at −20° C. Bile acids and sterols were determined by HPLC as described previously (Hong et al., 2007, J Agric Food Chem. 55:9750-7).

8.1.6. Statistical Analysis

All data are expressed as means±SE. Differences between control and different diet groups were determined by 2-tailed. Student's t tests. When variances of each group were unequal, significance of differences was determined using the Welch's test. Pearson correlation coefficients were calculated for investigating relationships of plasma total cholesterol, plasma adiponectin concentrations, hepatic cholesterol, and triglyceride concentrations with the expression of hepatic genes (JMP 7 statistical program, SAS Institute). Significance was defined at $P<0.05$.

8.2. Results

The animals fed Chardonnay seed flour had significantly decreased plasma levels of total cholesterol and LDL cholesterol compared to animals fed diets supplemented with commercially available grape seed extracts (FIGS. 18-19), with the exception of one of the groups fed a diet supplemented with Leucoselect® grape seed extract (L7). These data show that Chardonnay seed flour was superior to all but one of the commercial grape seed extracts tested for lowering total cholesterol and LDL cholesterol.

9. EXAMPLE 5: EFFECTS OF CHARDONNAY SEED FLOUR ON FECAL MICROBIOTA LEVELS 9.1. Materials & Methods 9.1.1. Fecal Samples Feces were collected from the animals of Example 1 at day 0 (control) and at day 20 (Chardonnay seed flour supplemented diet, Cabernet seed flour supplemented diet, and high-fat control diet). The feces were dried and frozen.

9.1.2. RNA Extraction and Quantification

Frozen fecal samples were added to 10 volumes of RNAlater®-ICE (Applied Biosystems, Foster City, Calif., USA) for at least 24 hours. Total RNA was prepared using the Stool Total RNA Purification Kit (Norgen Biotek Corp., Canada) following the manufacturer's protocols.

Quantity and purity of the isolated RNA was confirmed by spectrophotometry (A260/A280 ratio). cDNA was prepared for each sample using 250 ng of total RNA and a PrimeScript™ RT reagent kit (Takara Bio Inc., Shiga, Japan) according to the manufacturer's protocols.

Real-time PCR for quantification of intestinal bacterial 16S rRNA gene expression was performed using the AB 7500 Realtime PCR system (Applied Biosystems, Foster City, Calif., USA). Amplification was performed in duplicate using SYBR Premix Ex Taq (Takara Bio Inc., Shiga, Japan). Amplifications using the primers shown in Table 1 were performed with the following temperature profiles: one cycle at 95° C. for 30 seconds, and 40 cycles of denaturation at 95° C. for 5 to 10 seconds, annealating at the optimal temperature for 5 to 15 seconds and elongation at 72° C. for 20 seconds.

TABLE 1

| Target | Primer | Sequence(5' to 3') | Bacterial Strains for standard curve | SEQ ID NO |
|---|---|---|---|---|
| *Lactobacillus* spp. | Forward | AGCAGTAGGGAATCTTCCA | *Lactobacillus delbrueckii* subsp. *bulgaricus* (KCTC 3635) | 1 |
| | Reverse | CACCGCTACACATGGAG | | 2 |
| *Bifidobacterium* spp. | Forward | CTCCTGGAAACGGGTGG | *Bifidobacterium animalis* subsp. *lactis* (KCTC 5854) | 3 |
| | Reverse | GGTGTTCTTCCCGATATCTACA | | 4 |
| *Enterococcus* spp. | Forward | CCCTTATTGTTAGTTGCCATCATT | *Enterococcus faecalis* (KCTC 3206) | 5 |
| | Reverse | ACTCGTTGTACTTCCCATTGT | | 6 |
| *Clostridium* cluster IV | Forward | GCACAAGCAGTGGAGT | *Clostridium leptum* (KCTC 5155) | 7 |
| | Reverse | AGTSCTCTTGGGTAG | | 8 |
| *Pseudomonas aeruginosa* | Forward | CAAGCCCTACAAGAAATCCG | *Pseudomonas aeruginosa* (KCTC 1636) | 9 |
| | Reverse | TCCACCGAACCGAAGTTG | | 10 |
| *Staphylococcus aureus* | Forward | GCGATTGATGGTGATACGGTT | *Staphylococcus aureus* (ATCC 6538) | 11 |
| | Reverse | AGCCAAGCCTTGACGAACTAAAGC | | 12 |
| Total bacteria | Forward | TCCTACGGGAGGCAGCAGT | *Escherichia coli* (KCTC 1682) | 13 |
| | Reverse | GGACTACCAGGGTATCTAATCCTGTT | | 14 |

9.2. Results

The results of quantitative real-time PCR of the fecal samples of the hamsters fed a high fat diet containing Chardonnay or Cabernet seed flour revealed that the intestinal microbiota was modulated by the consumption of the flours. Measured total bacteria levels in fecal matter from hamsters fed the four diets are shown in FIG. 20. Measured levels of bacterial subpopulations are shown in FIGS. 21-26.

Fecal samples from hamsters fed a high-fat diet supplemented with Chardonnay seed flour showed significantly reduced levels of *Bifidobacterium* spp., *Lactobacillus* spp., and Enterobacteriaceae, and significantly increased levels of *Enterococcus* spp., bacteria of *Clostridium* cluster IV and the *Bacteroides fragilis* group compared to fecal samples from hamsters fed the high-fat control diet.

Fecal samples from hamsters fed a high-fat diet supplemented with Cabernet seed flour showed significantly reduced levels of Enterobacteriaceae, and significantly increased levels of *Enterococcus* spp., and the *Bacteroides fragilis* group compared to fecal samples from hamsters fed the high-fat control diet.

10. SPECIFIC EMBODIMENTS AND INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of treating metabolic syndrome in a mammal in need thereof comprising administering to the mammal in need thereof an effective amount of Chardonnay pomace flour.

2. The method of claim 1, wherein the treating metabolic syndrome reduces cholesterol of the mammal.

3. The method of claim 1, wherein the treating metabolic syndrome reduces the weight of the mammal.

4. The method of claim 1, wherein the treating metabolic syndrome reduces the weight of the liver of the mammal.

5. The method of claim 1, wherein the treating metabolic syndrome restores blood glucose levels to normal in the mammal.

6. The method of claim 1, wherein the mammal is a human.

7. A method of reducing the weight of a liver or reducing cholesterol in a mammal in need thereof comprising administering to the mammal in need thereof an effective amount of Chardonnay pomace flour.

8. The method of claim 7, wherein the method comprises reducing the weight of the liver in the mammal.

9. The method of claim 7, wherein the method comprises reducing cholesterol in the mammal.

10. The method of claim 7, wherein the mammal is a human.

11. A method of treating diabetes, increasing lipid metabolism, reducing weight, treating dyslipoproteinemia, increasing the amount of *Bacteroides fragilis* in the gut, decreasing the amount of Enterobacteriaceae bacteria in the gut, increasing the amount of *Clostridium* bacteria in the gut, or treating lactic acidosis in a mammal in need thereof, the method comprising administering to the mammal in need thereof an effective amount of Chardonnay pomace flour.

12. The method of claim 11, wherein the mammal is a human.

13. The method of claim 11, wherein the effective amount is at least 0.2 g/kg of body weight is administered to the mammal.

14. The method of claim 11, wherein the effective amount is at least 1.0 g per day is administered to the mammal.

15. A method of modulating total gut bacteria levels in the gut, the method comprising administering to a mammal an effective amount of Chardonnay pomace flour or Chardonnay pomace meal, thereby modulating the total gut bacteria levels in the gut.

16. The method of claim 15, wherein the method increases or decreases bacteria levels of a subset of the total gut bacteria in the mammal.

17. The method of claim 15, wherein the method further comprises administering an effective amount of Chardonnay seed extract.

18. The method of claim 15, wherein the mammal is a human.

* * * * *